(12) United States Patent
Mercolino

(10) Patent No.: US 12,377,025 B2
(45) Date of Patent: Aug. 5, 2025

(54) INTEGRATED DEVICE AND SYSTEM FOR REMOTE MEDICATIONS MANAGEMENT

(71) Applicant: Verinetics, Inc., Research Triangle Park, NC (US)

(72) Inventor: Thomas J. Mercolino, Chapel Hill, NC (US)

(73) Assignee: Verinetics, Inc., Research Triangle Park, NC (US)

( * ) Notice: Subject to any disclaimer, the term of this patent is extended or adjusted under 35 U.S.C. 154(b) by 252 days.

(21) Appl. No.: 18/150,960

(22) Filed: Jan. 6, 2023

(65) Prior Publication Data

US 2023/0147994 A1    May 11, 2023

Related U.S. Application Data

(63) Continuation-in-part of application No. 17/822,001, filed on Aug. 24, 2022, which is a
(Continued)

(51) Int. Cl.
*A61J 7/00* (2006.01)
*G07F 17/00* (2006.01)
*G16H 20/13* (2018.01)

(52) U.S. Cl.
CPC ........ *A61J 7/0076* (2013.01); *G07F 17/0092* (2013.01); *G16H 20/13* (2018.01)

(58) Field of Classification Search
CPC ........ G16H 20/13; G16H 40/67; G16H 40/63; G16H 40/40; A61J 1/03; A61J 7/0053;
(Continued)

(56) References Cited

U.S. PATENT DOCUMENTS 5,971,594 A    10/1999 Sahai
7,118,007 B1   10/2006 Yates
(Continued)

OTHER PUBLICATIONS

Uspto, Non-Final Office Action for U.S. Appl. No. 18/202,039, dated Jan. 9, 2024, 15 pages.
(Continued)

*Primary Examiner* — Michael Collins
(74) *Attorney, Agent, or Firm* — NK Patent Law

(57) ABSTRACT

The presently disclosed device includes a plurality of vials each bearing a unique identifier and in discrete locations in the device. An alignment assembly aligns one of the discrete locations with an access point for dispensing one of the vials. Computer executable instructions select a vial to be dispensed and store inventory information of the vials. The inventory information associates the unique identifiers with a status for each the plurality of vials indicating whether a vial is: loaded, dispensed, returned, or remaining undispensed in the device. The computer executable instructions also deactivate dispensing of the vials from the device based on at least one signal received from at least one environmental sensor configured to detect one of: location, temperature, humidity, vibration, shock, blood alcohol content (BAC), and light intrusion. A deactivation assembly deactivates dispensing of the vials based on the instructions.

13 Claims, 12 Drawing Sheets

Related U.S. Application Data continuation-in-part of application No. 17/245,028, filed on Apr. 30, 2021, now Pat. No. 11,676,693, which is a continuation-in-part of application No. PCT/US2019/058967, filed on Oct. 30, 2019.

(60) Provisional application No. 62/752,392, filed on Oct. 30, 2018.

(58) Field of Classification Search
CPC ........ A61J 7/04; A61J 7/0084; A61J 2200/30; A61J 7/0076; A61J 7/0427; G07F 17/0092; H04W 4/35; H04W 4/38
See application file for complete search history.

(56) References Cited

U.S. PATENT DOCUMENTS

| | | | |
|---|---|---|---|
| 8,108,068 B1* | 1/2012 | Boucher | G01G 17/00 700/240 |
| 9,889,069 B1 | 2/2018 | Coe | |
| 10,073,954 B2 | 9/2018 | Chen | |
| 10,265,245 B2* | 4/2019 | Kraft | G16H 20/13 |
| 10,426,707 B2 | 10/2019 | Hsu | |
| 10,597,206 B2 | 3/2020 | Corey | |
| 10,821,054 B1 | 11/2020 | Howton | |
| 11,676,693 B2* | 6/2023 | Mercolino | G16H 40/67 700/236 |
| 11,771,693 B2* | 10/2023 | Iorio | A61J 1/1437 604/890.1 |
| 12,102,604 B1* | 10/2024 | Robinson | A61J 1/16 |
| 2007/0023444 A1 | 2/2007 | Holloway | |
| 2010/0318218 A1* | 12/2010 | Muncy, Jr. | G16H 20/13 221/199 |
| 2011/0226817 A1 | 9/2011 | Ortenzi | |
| 2013/0090594 A1 | 4/2013 | Palmer | |
| 2013/0110283 A1 | 5/2013 | Baarman | |
| 2016/0158107 A1* | 6/2016 | Dvorak | A61J 7/0084 221/9 |
| 2017/0326033 A1* | 11/2017 | Kraft | G16H 40/67 |
| 2018/0130050 A1* | 5/2018 | Taylor | G06Q 20/065 |
| 2018/0285880 A1 | 10/2018 | Jerstroem | |
| 2019/0295350 A1 | 9/2019 | Wegelin | |
| 2020/0279632 A1 | 9/2020 | Mercolino | |
| 2021/0249112 A1 | 8/2021 | Mercolino | |
| 2022/0063883 A1 | 3/2022 | Mott | |
| 2022/0230723 A1 | 7/2022 | Wieczorek et al. | |
| 2022/0402696 A1 | 12/2022 | Mercolino | |
| 2023/0298723 A1* | 9/2023 | Mercolino | G16H 10/60 700/236 |

OTHER PUBLICATIONS

USPTO, Final Office Action for U.S. Appl. No. 18/202,039, dated Jun. 27, 2024, 8 pages.

Uspto, Non-Final Office Action for corresponding U.S. Appl. No. 17/822,001, dated Dec. 9, 2024, 9 pages.

USPTO, Final Office Action for corresponding U.S. Appl. No. 17/822,001, dated May 30, 2025, 11 pages.

* cited by examiner

INTEGRATED DEVICE AND SYSTEM FOR REMOTE MEDICATIONS MANAGEMENT

CROSS REFERENCE TO RELATED APPLICATIONS

This application is a continuation-in-part of U.S. patent application Ser. No. 17/822,001 entitled "Integrated Device and System for Drug Dispensing," which was filed on Aug. 24, 2022, which is a continuation-in-part of U.S. patent application Ser. No. 17/245,028 entitled "Integrated Device and System for Drug Dispensing," which was filed on Apr. 30, 2021, which is a continuation-in-part of PCT Patent Application No. PCT/US2019/058967 entitled "AN INTEGRATED DEVICE AND SYSTEM FOR DRUG DISPENSING," which was filed on Oct. 30, 2019, which claims benefit of and priority to U.S. Provisional Patent Application No. 62/752,392 entitled "INTEGRATED DEVICE AND SYSTEM FOR DRUG DETECTION AND DEACTIVATION TO DETER CONTROLLED SUBSTANCE THEFT IN HOSPITALS AND OTHER HEALTHCARE DELIVERY SETTINGS," which was filed on Oct. 30, 2018, the contents of all of which are incorporated by reference herein.

TECHNICAL FIELD

The present invention relates to systems, methods, and devices remote medications management.

BACKGROUND

Controlled substance drugs (CS drugs) are those subject to restrictions on distribution, dispensing, and disposal by government agencies.

For example, without limitation, such restrictions apply to many therapeutic products for which the US Food and Drug Administration's (FDA) requires a prescription for dispensing. Additionally, the under the authority of The Controlled Substances Act places all pharmaceuticals products into one of five schedules. Pharmaceuticals are scheduled as a CS if they have "potential for abuse", as indicated by: evidence that individuals are taking the drug such that it is a hazard to themselves or others; significant diversion from legitimate drug channels; individuals taking the drug without medical advice; or, a new drug or drug in testing with similar pharmacology to a drug having abuse potential. Included in the most restrictive Schedule II category are narcotic analgesics, prescriptions for which must be written and signed by the practitioner and may not be refilled.

Moreover, restrictions on distribution, dispensing, and disposal apply to investigational new drugs in clinical testing. For example, a clinical investigator may administer such drug only to subjects under the investigator's personal supervision or under the supervision of a subinvestigator responsible to the investigator, and the investigator may not supply the investigational drug to any person not authorized to receive it.

The distribution and dispensing of cannabis, whether legal for recreational use, medicinal use, or both, is controlled by government agencies.

Medicated-Assisted Treatment (MAT) is the use of FDA-approved medications, often in combination with counseling and behavioral therapies, to provide a "whole-patient" approach to the treatment of substance use disorders. Two medications (methadone and buprenorphine) commonly used to treat opioid addiction are CS drugs, themselves. It is desirable and sometimes required by law that the license medical practitioner who provides MAT do so in a "qualified practice setting." A qualified practice setting is one that ideally provides: professional coverage for patient medical emergencies during hours when the practitioner's practice is closed; access to case-management services for patients including referral and follow-up services, such as medical, behavioral, social, housing, employment, educational, or other related services; uses health information technology systems such as electronic health records; and, is registered for their US State prescription drug monitoring program (PDMP) where operational and in accordance with US Federal and State law.

Many patients may not qualify for at-home dispensing of controlled substances. For example, a patient may live in a group home, or have several children at home, and the patient may be a new patient and lack a history of successful at-home dosing. A lack of physical security at the home where people other than the patient may try and access the controlled substance may dissuade a clinic from allowing at-home dispensing of the controlled substance for that patient. In another example, an older patient may be forgetful about taking the controlled substance or physically securing the controlled substance using conventional methods. Again, a clinic may be dissuaded from allowing at-home dispensing for such a patient. A disadvantage of current systems for dispensing controlled substances is that each clinic can only support a certain number of in-person patients. Yet patients who may otherwise qualify for at-home dosing may not allowed at-home dispensing due to clinic concerns of potential abuse.

It desirable that access to outpatient care, including in home settings, qualify for some or all the ideal aspects of a qualified practice setting given above. Accordingly, there remains a need to address these disadvantages and others not described herein.

BRIEF DESCRIPTION OF THE DRAWINGS

The present embodiments are illustrated by way of example and are not intended to be limited by the figures of the accompanying drawings. In the drawings.

The same reference numbers and any acronyms identify elements or acts with the same or similar structure or functionality throughout the drawings and specification for ease of understanding and convenience.

DETAILED DESCRIPTION

Figure 1:
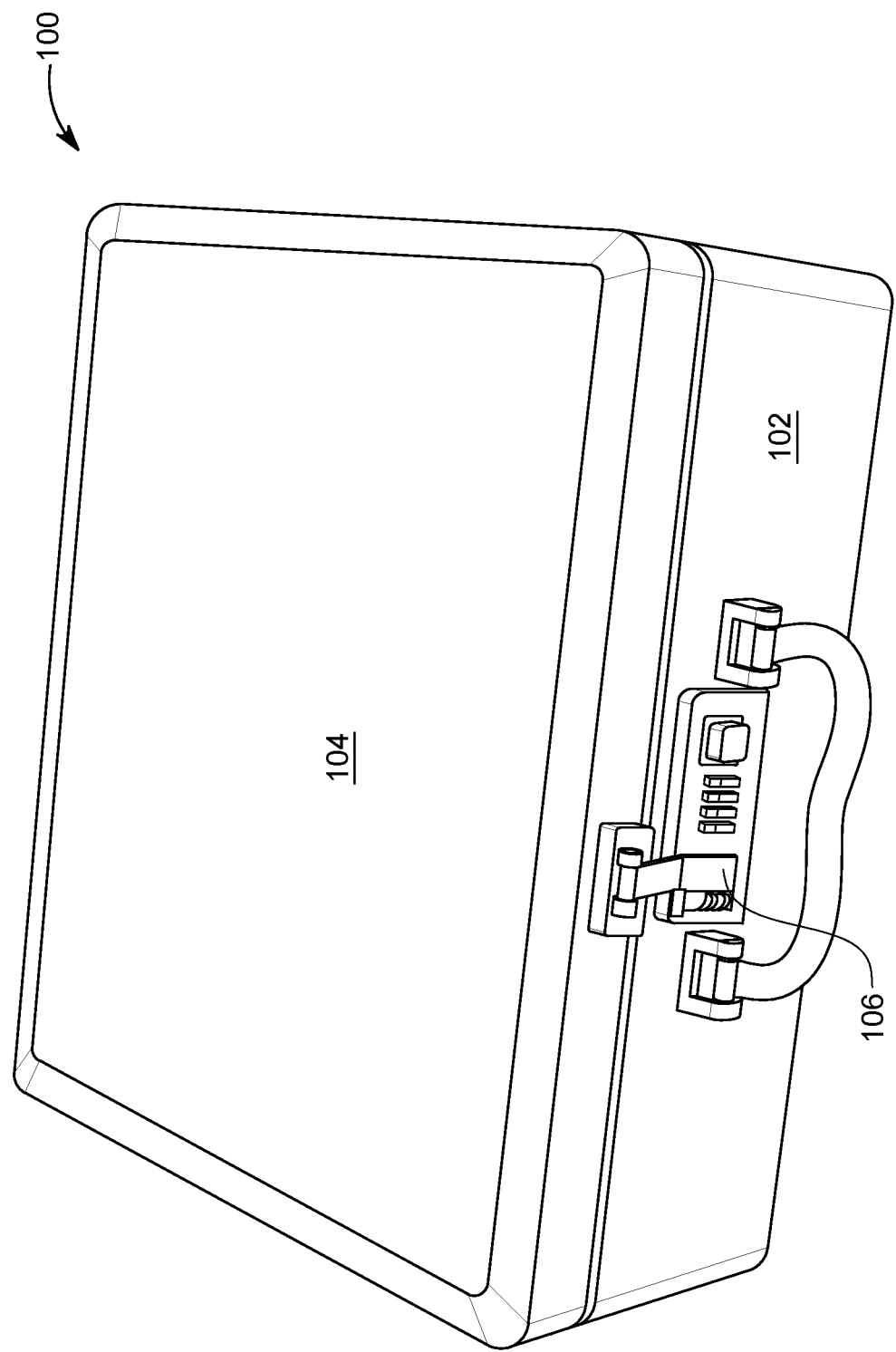
FIG. 1 depicts a network-enabled lockbox for remote medications management to an embodiment of the subject matter described herein.

Techniques are disclosed for secure dispensing of substances, such as controlled substances. As used herein, a "controlled substance" is viewed broadly and refers to any drug or other substance that is controlled by a government agency. Certain such controlled substances may be more tightly controlled because they may be abused or cause addiction. The control applies to the way the substance is made, used, handled, stored, and distributed. Controlled substances include opioids, stimulants, depressants, hallucinogens, and anabolic steroids. Controlled substances with known medical use, such as methadone, morphine, Valium, and Ritalin, are available only by prescription from a licensed medical professional. Likewise, drugs under clinical investigation are controlled and considered herein as controlled substances.

The presently disclosed device includes a plurality of vials each bearing a unique identifier and in discrete locations in the device. An alignment assembly aligns one of the discrete locations with an access point for dispensing one of the vials. Computer executable instructions select a vial to be dispensed and store inventory information of the vials. The inventory information associates the unique identifiers with a status for each the plurality of vials indicating whether a vial is: loaded, dispensed, returned, or remaining undispensed in the device. The computer executable instructions also deactivate dispensing of the vials from the device based on at least one signal received from at least one environmental sensor configured to detect one of: location, temperature, humidity, vibration, shock, and light intrusion. A deactivation assembly deactivates dispensing of the vials based on the instructions.

In one embodiment, a network-enabled lockbox for remote medications management includes a wireless communication device, one or more sensors, and a rotating carousel containing one or more doses of the substance. The carousel is configured to provide a dose of the substance during a preconfigured period of time. The one or more sensors are configured to detect one or more alert conditions. The wireless communications are configured to wirelessly communicate information between the network-enabled lockbox and a remote server. Detecting an alert condition may be configured to cause an alarm condition to be registered on the remote server. Detecting an alert condition also may be configured to disable the lockbox dispensing function, either local and autonomously or in response the remote server having registered an alarm condition. In another embodiment, dispensing functions of a network-enabled lockbox are disabled by a signal initiated manually at the remote server.

In another embodiment, a network-enabled lockbox for remote medications management includes an outer compartment, an interior frame inserted into the compartment and secured to the compartment, a top plate, a worm drive, an electric motor connected to the worm drive, control electronics for controlling the motor, a carousel connected to the worm drive, a plurality of sensors, and a communications subsystem for communicating data to a backend server.

The outer compartment includes a body and a lid pivotably coupled to the body for selectively opening the compartment, where a space enclosed by the compartment is physically secured with a lock built-in to the compartment or attached with security screws that cannot be removed from the exterior of the lid or can only be removed with a special tool.

The interior frame includes a shield/divider for physically separating a first portion of the space enclosed by the compartment from a second portion of the space enclosed by the compartment. The interior frame includes a static dose compartment includes four side walls for storing a static dose of the substance. The interior frame includes a motor housing surrounding the motor and the worm drive for physically separating and enclosing the motor and the worm drive in a third portion of the space enclosed by the compartment, wherein motor housing is securely attached to the compartment.

The worm drive includes an input shaft and an output shaft. The input shaft includes a cylinder having a spiral thread that engages with and drives a toothed wheel. The output shaft includes a cylinder attached to the toothed wheel, where the output shaft is connected to the carousel for rotating the carousel. A gear ratio of the worm drive is configured so that the direction of transmission between the input shaft and the output shaft is not reversible.

The electric motor is connected to the input shaft of the worm drive, the battery, and the control electronics, where the electric motor is powered by the battery and drives the input shaft based on instructions from the control electronics.

The carousel includes a top plate and a bottom plate, each plate including a circular disc of material. The bottom plate has an inner diameter and an outer diameter where a solid material is located between the inner and outer diameters. The bottom plate also has a plurality of screw holes for receiving a plurality of standoff screws that securely attach the bottom plate to the top plate. The top plate has an inner diameter and an outer diameter where a solid material is located between the inner and outer diameters. The inner diameter is configured for receiving the output shaft. The top plate includes a solid material located between the inner and outer diameters. The top plate further has a plurality of non-overlapping dispensing positions, where every dispensing position except one includes a hole for receiving a dose of the substance. The dispensing positions are equally spaced from each other, the top plate also having a plurality of screw holes for receiving a plurality of standoff screws for securely attaching the top plate to the bottom plate.

A battery is connected to the motor and other electronic components for providing electrical power to the motor, the control electronics, the communications electronics, and the plurality of sensors. The battery is further connected to an input plug for receiving electrical power from an external power source.

A communications subsystem communicates data between the plurality of sensors and/or the control electronics and a backend server and/or a mobile device. The communications subsystem includes a Wi-Fi device for communicating with nearby digital devices to exchange data by radio waves via IEEE 802.11 wireless network protocols. The communications subsystem also includes cellular radio for communicating wirelessly with cellular network towers. The communications subsystem also includes a Bluetooth device for exchanging data between over short distances using UHF radio waves in the ISM bands from 2.402 GHz to 2.48 GHz.

Control electronics are connected to the battery for controlling the motor. The control electronics include a memory and a processor for storing and executing instructions. The instructions can be configured locally or remotely.

A plurality of sensors is connected to one or more of the control electronics, the communications subsystem, and the battery. The plurality of sensors include at least one of: a location sensor for determining a location of the network-enabled lockbox, wherein the location sensor includes a global positioning system (GPS) device; a temperature sensor for measuring a temperature of at least one of a volume of air or a physical component of the network-enabled lockbox; a humidity sensor for detecting and measuring water vapor within a volume of air; an accelerometer for measuring a rate of change of a velocity of the network-enabled lockbox; a visual sensor, wherein the visual sensor is a camera; an audio sensor, wherein the audio sensor is a microphone; and a plurality of proximity sensors for detecting presence of nearby objects without physical contact. The plurality of proximity sensors include at least one of: a first access port sensor for sensing whether the first access port lid is in an open position or a closed position; a second access port sensor for sensing whether second access port lid is in an open position or a closed position; a top cover sensor for sensing whether the top cover is in an open position or a closed position; a lid lock sensor for sensing whether the lid is in a locked position or an unlocked position; and a top cover lock sensor for sensing whether the top cover is in a locked position or an unlocked position. The one or more of the proximity sensors includes a magnetic contact sensor that is configured to identify the closed position or the locked position when a magnetic field is above a threshold value and to identify the open position or an unlocked position when the magnetic field is below a threshold value.

A top cover covers the carousel, the interior frame, the worm drive, the motor, the battery, the control electronics, and the communications subsystem and the top cover is securely attached to the compartment. The top cover includes a first access port comprising a first opening in the top cover and a first access port lid pivotably coupled to top cover and covering the first opening, wherein the first access port is aligned with one of the dispensing positions. The top cover includes a second access port comprising a second opening in the top cover and a second access port lid pivotably coupled to top cover and covering the second opening, wherein the second access port is aligned with an open portion of the static dose compartment.

Among other advantages, embodiments disclosed herein enable for remote monitoring and control of the dispensing of substances, especially controlled substances. This allows more patients to receive their medications at home without going into a clinic or dispensary in person without introducing unwanted security risks including, but not limited to, physical security of the controlled substance doses from tampering by persons other than the patient and overdosing.

In an exemplary embodiment, the network-enabled lockbox is an Internet of Things (IoT)-enabled dispenser designed to hold controlled substance medications. The dispenser has imbedded LTE-M radio and communicates with a remote software application hosted in the cloud. The dispenser has autonomous logic on-board to execute patient dosing orders even when not connected to the remote application.

The dispenser has physical dimensions: height, width, length, and weight. The dispenser consists of a bottom that holds medications and electronics, which are hidden with a lockable top plate. The top of the dispenser is connected via hinges to the bottom of the dispenser and contains a 4-digit combination lock.

Inside the dispenser, the top plate includes a button, a display, and hole for taking one scheduled dose from the dispenser compartment which is covered by a door, opening or closing of which is detected by a sensor. Inside the dispenser is also a dispenser compartment for taking an unscheduled safety or static dose, which may be the last dose of a cycle but can also be an emergency or safety dose, which is covered by a sensored cover.

Device capacity is 13 doses (up to 12 doses in the carousel and one static dose. A rotating carousel inside the dispenser can have one blank position which can be filled with a stub. The blank position, if configured, can be exposed: after the device refilled, before the first dose, and/or between doses. For maintenance purposes (e.g., filling the dispenser), the top cover can be opened. Main functions of the dispenser include: physical security and control of medication, provider-determined remote medication dosing protocol, and near real-time medication usage and inventory.

The following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be, but not necessarily are, references to the same embodiment; and such references mean at least one of the embodiments.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way.

Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only and is not intended to further limit the scope and meaning of the disclosure or of any exemplified term. Likewise, the disclosure is not limited to various embodiments given in this specification.

Without intent to limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions will control.

As used herein, an article is a physical object on which a label may be applied. Examples of articles would include a vial, a capsule, a solid oral dosage form, a prefilled syringe, personal property, electronics, etc.

As used herein, a vial is an article that may be used to hold a physical object, a plurality of physical objects, or a liquid. A vial may be capped or otherwise sealed, uncapped or unsealed. "Vials" also may be removable cups whether capped, sealed, or unsealed.

FIG. 1 depicts a network-enabled lockbox 100 for remote medications management according to an embodiment of the subject matter described herein. The network-enabled lockbox 100 is shown in a closed and fully secured position. The network-enabled lockbox 100 includes an outer compartment, shell, or case including a body 102 and a lid 104. The lid 104 is pivotably coupled to the body 102 for selectively opening the compartment 100. An interior space enclosed by the compartment is physically secured with a keyless lock 106 built-in to the body 102. The lock 106 may be an alphanumeric combination lock, a biometric lock, or a network-enabled lock that communicates via Bluetooth with an authorized and authenticated mobile device. The body 102 and the lid 104 may be composed of a solid material, such as metal or plastic, for physically obscuring and securing the contents therein. Additionally, the body 102 and the lid 104 may provide temperature and humidity control to the contents therein both for protecting the integrity of the controlled substance doses and the various electronics and communications equipment stored therein.

Figure 2:
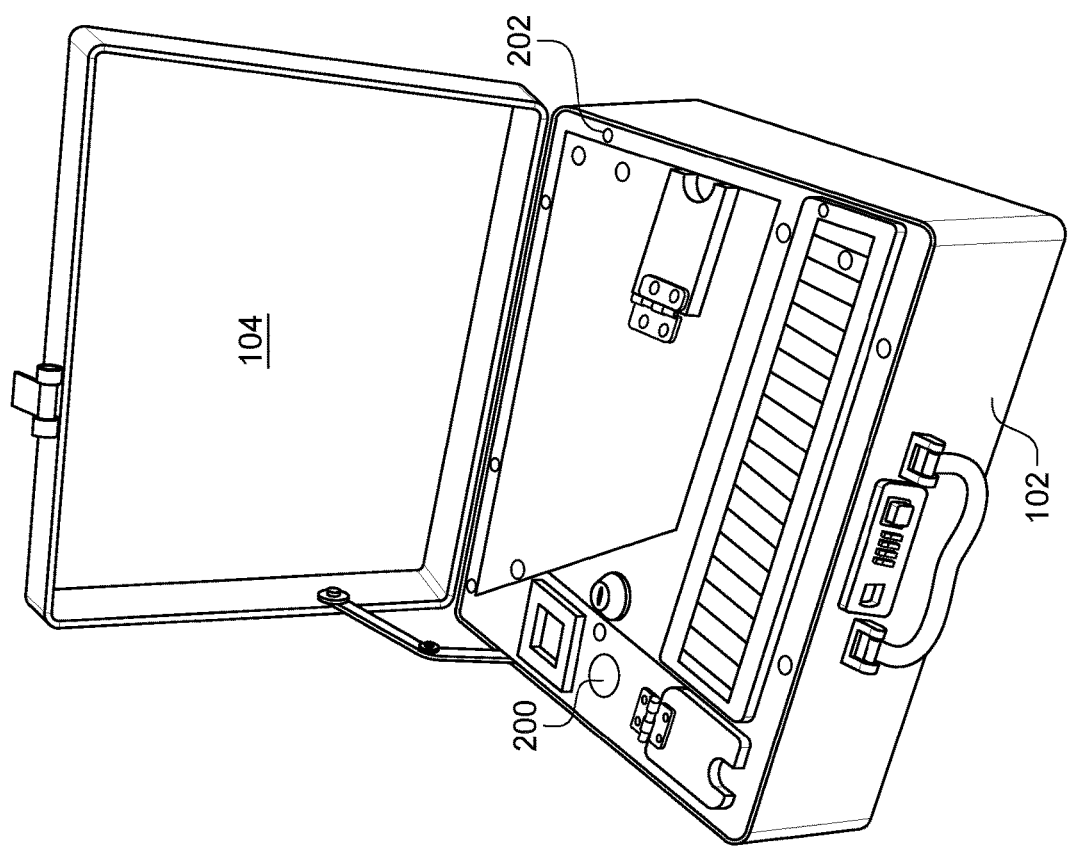
FIG. 2 depicts a network-enabled lockbox for remote medications management including dispensing a substance with the lid open thereby exposing the top plate where all dispensing lids are in a closed position according to an embodiment of the subject matter described herein.

FIG. 2 depicts a network-enabled lockbox for remote medications management with the lid open and all dispensing lids in a closed position according to an embodiment of the subject matter described herein. For example, once a user successfully opens the built-in lock 106, the lid 104 may pivotably hinge and expose an interior of the case. As shown in FIG. 2, all dispensing lids are in a closed position. This may occur because the time at which the lid 104 is opened was not during a preconfigured dispense window (DW). A dispense window is a period of time, such as ten minutes from 8:00 am until 8:10 am each day, during which a dose or vial of the controlled substance is configured to be made available to the user. The DW may be configured to remain open continuously. Outside the DW, the primary access port lid is closed and inside the DW the primary access port lid is open. The DW may be determined when the lockbox 100 is loaded and secured, for example at a clinic dispensary. The DW may be defined by a unit dispensing start date, an interval in hours, a number of carousel slots filled with medical doses, and a dosage window allotted time allocation in minutes.

A top cover 200 cover provides physical security to the contents of the lockbox 100 when the lid 104 is open. The top cover 200 is securely attached to the compartment. For example, a plurality of screws may attach the top cover 200 to various mounting points located on the body 102. The top cover 200 may be composed of a solid material, such as metal or plastic, for physically obscuring and securing the contents therein. Alternatively, the top cover 200 may be composed of a transparent material to allow visibility to the contents.

Figure 3:
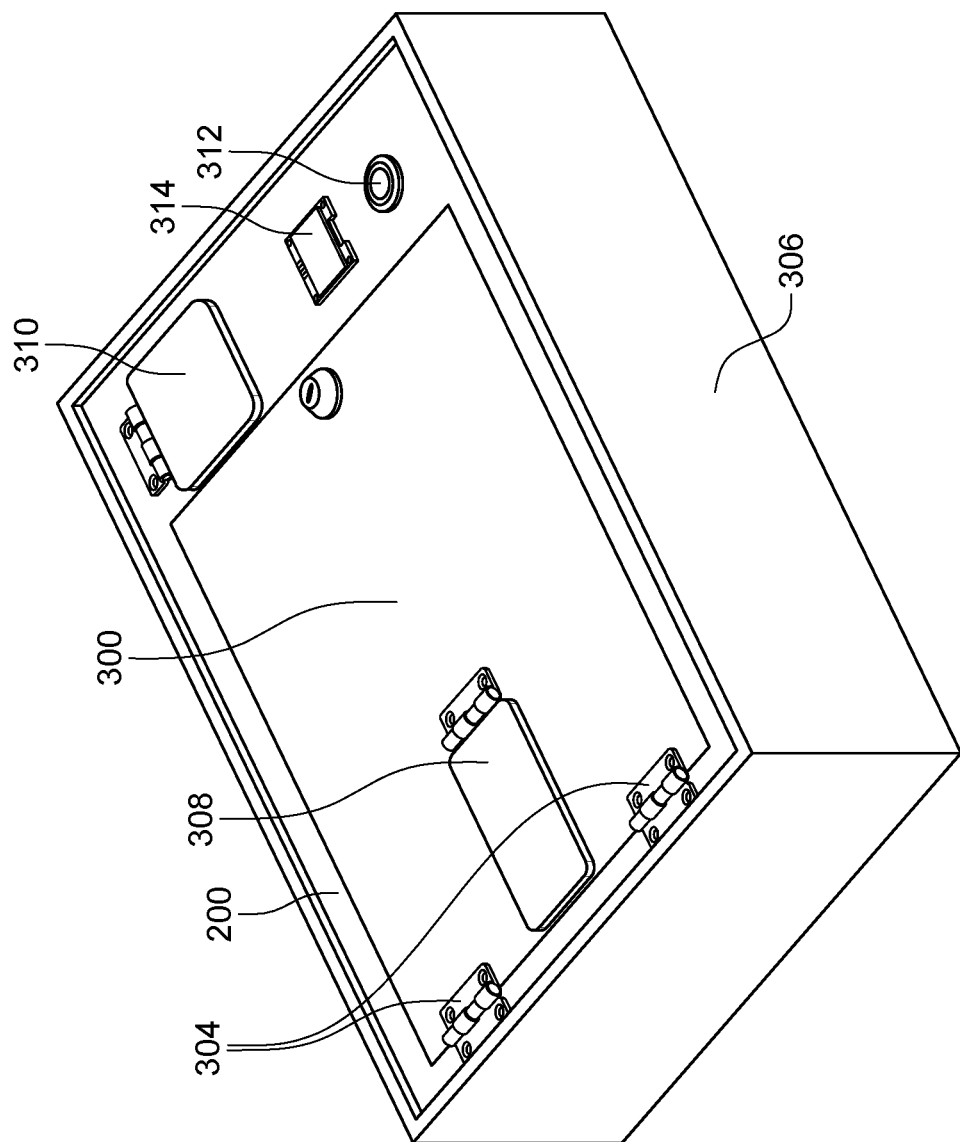
FIG. 3 depicts the top plate of the network-enabled lockbox for remote medications management in greater detail according to an embodiment of the subject matter described herein.

FIG. 3 depicts the top plate of the network-enabled lockbox for remote medications management in greater detail according to an embodiment of the subject matter described herein. The top cover 200 may be include a carousel cover 300 that is pivotably hinged using hinges 302 to the top cover 200 and secured with a lock 304. This allows an administrator to access the carousel (e.g., for repair or loading/unloading of vials) without removing the entire top plate 200. The top plate 200 may be secured to a box 304 via screws. The screws may be associated with one or more sensors for detecting unauthorize attempts to remove the top plate.

The top cover 200 includes a first access port 308, also referred to as a primary dispensing door or main dispensing door, that includes a first opening in the top cover 200 and a first access port lid pivotably coupled to the top cover 200 that covers the first opening. The first access port 308 is aligned with a dispensing position, which will be described in greater detail below.

The top cover 200 also includes a second access port 310, also referred to as a static dose dispensing door, comprising a second opening in the top cover 200 and a second access port lid that is pivotably coupled to the top cover 200 and covers the second opening. The second access port 204 is aligned with an open portion of the static dose compartment, which will be described in greater detail below.

The top cover 200 includes a dosing button (DB) 312. The dosing button 312 is used to activate (e.g., unlock or open) the first access port lid 308 during the DW (or the second access port lid 310 regardless of the DW). The dosing button 312 may incorporate colored lights and/or speakers to indicate various states or conditions of the lockbox 100 to the user. For example, if the top cover 200 is opened outside of the DW, the dosing button 312 color may be red. When the DW is reached, the lockbox 100 may play a sound and the dosing button 312 may be green. When the dosing button 312 is pressed, the motor may move the carousel to next position and the dosing button 312 may be blue. After dosing is complete and the first access port lid 308 is closed, power to the dosing button 206 may be reduced and/or the dosing button 206 may be or turned off.

The top cover 200 includes an information display screen 314 for displaying various notifications to the user. For example, if the top cover 200 is opened outside of the DW, the display screen 314 may display a message such as "Next dosing is scheduled for 2021-09-13 6:00 PM". When the DW is reached, the display screen 314 may display: "For next dose, press the button". When the dosing button 312 is pressed, the display screen 314 may display: "Dose is ready, please take a dose". When the patient removes the bottle of medicine from the lockbox 100 (e.g., as detected by a first access port lid 308 sensor that assumes the first access port lid closes after removing full bottle), a message may be displayed on the display screen 314: "Return empty dose and push button to confirm". Once the empty bottle is returned to the device (e.g., as detected by the first access port lid 308 sensor and confirmed with the button), a message may be displayed on the display screen 314: "Dosing completed, please close and lock the lid". After dosing is complete and the first access port lid 308 is closed, power to the display screen 314 may be reduced and/or the display screen 314 may be or turned off.

Sensors:

The lockbox 100 may include a plurality of sensors. These sensors may be variously connected to one or more of the control electronics, the communications subsystem, and the battery. The plurality of sensors can include: a location sensor for determining a location of the network-enabled lockbox (e.g., a global positioning system (GPS) device), a temperature sensor for measuring a temperature of at least one of a volume of air or a physical component of the network-enabled lockbox, a humidity sensor for detecting and measuring water vapor within a volume of air, an accelerometer for measuring a rate of change of a velocity of the network-enabled lockbox, a visual sensor (e.g., a camera), an audio sensor (e.g., a microphone), and proximity sensors for detecting presence of nearby objects without physical contact. The proximity sensors may include: a first access port sensor for sensing whether the first access port lid is in an open position or a closed position, a second access port sensor for sensing whether second access port lid is in an open position or a closed position, a top cover sensor for sensing whether the top cover is in an open position or a closed position, a lid lock sensor for sensing whether the lid is in a locked position or an unlocked position, and a top cover lock sensor for sensing whether the top cover is in a locked position or an unlocked position. The proximity sensor may include a magnetic contact sensor that is configured to identify the closed position or the locked position when a magnetic field is above a threshold value and to identify the open position or an unlocked position when the magnetic field is below a threshold value.

It is appreciated that in addition to the humidity sensor for detecting and measuring water vapor within a volume of air may, the sensor can also include a breathalyzer or similar device. A breathalyzer (a portmanteau of breath and analyzer) is a device for estimating blood alcohol content (BAC), or to detect viruses or diseases from a breath sample. The diagnostic device estimates a person's BAC by blowing into the device. When the user exhales into the breath analyzer, any ethanol present in their breath is oxidized to acetic acid at the anode, atmospheric oxygen is reduced at the cathode, and the overall reaction is the oxidation of ethanol to acetic acid and water. The electric current produced by this reaction is measured by a microcontroller and displayed as an approximation of overall BAC.

The breathalyzer sensor may be used to allow or deny access to the lockbox 100. For example, a person with a BAC above a threshold amount (e.g., 0), as measured by the breathalyzer, may be automatically prevented from accessing the lockbox 100. Additionally, the results of the breathalyzer test may be automatically transmitted to a remote server to notify, for example, the person's doctor or other entity. Conversely, access to the lockbox 100 may be allowed if, as one of one or more possible conditions, the user passes the breathalyzer test.

The lockbox 100 disclosed herein, being a physically and electronically secured medications management dispenser is an Internet of Things (IoT) connected device. In one embodiment, it is also linked via Bluetooth to a user's (e.g., a Veteran's) smart watch for monitoring vital signs relevant to potential distress. The smart watch may also serve as a proximity sensor for locking out dispensing to unintended users. As mentioned above, when the lockbox 100 is linked to a breathalyzer and alcohol use is above a critical threshold, medications will not dispense. If any distress is detected, the lockbox 100 can send "push" signals to a paired mobile device to automatically open apps, like a Veterans Crisis Line (VCL). Alternatively, a mobile device counseling session may be required before unlocking medication dispensing. Lockbox 100 status information, including user behavior associated with medication dispensing requests may be communicated in real time via mobile network to cloud-based data management and analytics software with dashboard presentation to caregivers.

The system disclosed herein can notify caregivers of acute suicide risk. To achieve this, the lockbox 100 may act as a local network hub for monitoring measures of a user's behavioral, physiological, and social determinants of health and wellbeing associated with suicide risk. In the system, a smart watch can monitor user proximity to the dispenser, unlocking dispensing only when the user is nearby. The watch may also monitor physiologic markers like heartrate, oxygenation state (pO2), blood pressure (BP), and electrocardiogram (ECG). Since alcohol use would contribute to the potential lethality of dispensed drugs, the system disclosed herein may be connected to a mobile breathalyzer, locking out drug dispensing above a pre-set blood alcohol level. Should any measure associated with acute suicide risk exceed a configurable pre-set threshold, the system disclosed herein may autonomously lock out dispensing and notify the user's caregiver to achieve intervention in a right-care, right-time, right-place approach. The triggering thresholds may be configured at different levels based upon a user's risk of attempting suicide.

The system disclosed herein can improve access to suicide prevention resources by providing links to mobile technology and applications. This allows the system disclosed herein to integrate, in real time, with existing digital health initiatives such as the VCL. Improving access to the relevant resources is accomplished through "push" notifications to a user's mobile device triggered by specific events (e.g., high blood alcohol content). The system disclosed herein also can trigger a "push" notification requiring a response before unlocking medications. These required responses can be set to a recurring schedule or linked a simple survey question, like a mandatory yes vs. no answer to the question, "Have you had thoughts about taking your life?" A follow up connection to VCL, including a counseling encounter, can also be configured depending upon the response.

Finally, the system disclosed herein may collect conjoined passive data about a user's at-home use of medications and active physiological data indicating an individual user's suicidality. The system disclosed herein also passively collects data about user's self-dosing behavior at home (e.g., time of day, frequency of requests, location, etc.) in conjunction with physiologic markers (e.g., heart rate, pO2, BP, BAC, screening questions), both baseline and as the user approaches the lockbox 100 anticipating drug dispensing. Evidence for alcohol use also can be measured in conjunction with other factors. Passive and active conjoined data can further refine and individual user's suicide risk, yielding predictors of agitation, depression, suicidality, and other relevant risk factors.

Environmental sensors: Environmental sensors can detect temperature and humidity, either absolute values or relative changes. This information can be reported to a back-end server as an "event" where an event may occur when the temperature and/or humidity detected by the environmental sensors is outside of a threshold value or range. For example, before start of dosing, the device may send a "heartbeat" event (as discussed below) to the server to check if device is locked from server side. Environmental sensor data may also be sent from the device to the server with this event.

GPS: GPS can be configured to activate after a defined period of device load/reload. For example, a default value may be configured such as one hour. GPS can also be configured to send data to the server 902 at specified intervals after the load/reload interval. Once an hour is also the default interval for GPS messages sent to the server. Once active GPS sensing and message sending also occurs at the start and end of the DW If positions are available.

Accelerometer: This sensor may include an acceleration sensor and a gyroscope sensor. The accelerometer may be active all the time. The accelerometer can detect free fall and shock to device. In case of one or both of those events, the device can be automatically locked and reported to server. The device may stay locked until a remote unlock signal is sent to the device from the server.

Intrusion sensor: If the dispenser is not in a load/unload state, the intrusion sensor can detect that the top plate 200 is removed from the dispenser. In this event, the device may send a message to the server and lock the dispenser.

Static dose cover opening detection sensor: This sensor can detect that the static dose compartment 310 is opened and report event to the server.

Lid opening sensor: This sensor can detect that the lid 102 is opened. In that circumstance the dispenser will report a "lid open" event to server.

In summary, sensors on the lockbox 100 can include touch screen keypad (including single touch, multi-touch, gesture sensing in 2D or 3D, etc.), a physical keypad, a mouse, a pointer, a track pad, a stylus, a stylus detector/sensor/receptor, motion detector/sensor (e.g., including 1-axis, 2-axis, 3-axis accelerometer, etc.), a face detector/recognizer, a retinal detector/scanner, a light sensor, capacitance sensor, resistance sensor, temperature sensor, proximity sensor, a piezoelectric device, device orientation detector (e.g., electronic compass, tilt sensor, rotation sensor, gyroscope, accelerometer), or any combination of the above.

Signals received or detected at the lockbox 100 through one or more of the above input mechanisms, or others, can be used in the disclosed technology in obtaining context awareness at the lockbox 100. Context awareness at the lockbox 100 generally includes, by way of example but not limitation, the lockbox 100 operation or state acknowledgement, management, user activity/behavior/interaction awareness, detection, sensing, tracking, trending, and/or application (e.g., mobile applications) type, behavior, activity, operating state, etc. Context awareness information may be sent to the back-end server on a predefined schedule, or "heartbeat". The heartbeat may contain some or all event information or may be a single information packet designating no change in operation or state since last heartbeat.

Client-side software components can include software or agents installed on the lockbox 100 that enables and performs functionalities on the lockbox 100. The client-side software components can perform administrative functions such as receiving service requests and policy updates from the server 902. Example client-side software components are discussed below.

Device State Monitor: A device state monitor can be responsible for identifying various states and metrics of the lockbox 100, such as network status, display status, battery level, etc. such that other client-side software components can operate and make decisions according to the device state.

Reporting Agent: A reporting agent can gather information about the events taking place in the lockbox 100 and send the information to the backend server. Event details may be stored temporarily in the lockbox 100 and transferred to the server when a data channel is active or open. This may be based on a preconfigured schedule or may be pushed automatically. Additionally, if the client-side reporting agent fails to send an expected record within a preconfigured time frame (e.g., twenty-four hours), the server may attempt to open a connection retrieve any records.

Reporting and Usage Analytics Component: A reporting and usage analytics component can collect information from the lockbox 100 and provide this information to the server. Software executing on a remote computer may access the reported information to produce reports that operators can use for analyzing usage of the lockbox 100.

In summary, Table 1 below is an exemplary list of components of the lockbox 100, their function(s), and whether the component is associated with a sensor and/or an action.

| Component name | Function | Actions Sensed Y/N? |
|---|---|---|
| Printed circuit board (PCB) | Electronic circuit used in devices to provide mechanical support and a pathway to its electronic components. | Y |
| LilyGO TTGO T-SIM7000G Module | Micro controller unit (MCU); wireless communications | Y |
| GPS Antenna | Receiving and expanding radio signals sent by distinct frequencies from GPS satellites. | N |

-continued

| Component name | Function | Actions Sensed Y/N? |
|---|---|---|
| LTE-M Antenna | Sending and receiving LTE-M radio signals. LTE-M (Long Term Evolution (4G), category M1) is for Internet of Things (IoT) devices to connect directly to a 4G network, without a gateway and on batteries. | Y |
| SIM card | Subscriber identity module (SIM), or subscriber identification module (SIM), is an integrated circuit running a card operating system (COS) that is intended to securely store the international mobile subscriber identity (IMSI) number and its related key, which are used to identify and authenticate mobile devices. | Y |
| DC motor with gearbox w/locking mechanism and encoder | Carousel moving and locking | Y |
| Dispense button | Patient actions button | Y |
| LED Display 1.3" | Human machine interface (HMI); displaying visual information. | |
| Wiring set | Electrical connection. | |
| Battery pack | Power supply | Y |
| Carousel plates set for 12 slot carousels | Bottles holding and movement | |
| Carousel standoffs set | Carousel mounting | |
| Carousel gear | Coupling between carousel and motor shaft | |
| Case open sensor | Detection of case opening event | Y |
| Intrusion detection sensor | Detection of top plate removal | Y |
| Static dose cover opening detection sensor | Detection of static dose compartment opening | Y |
| Case with 4-digit lid lock and bottom | Physical enclosure and security of internal elements. | Y |
| Dosing door sensor | Detection of taking out/returning of bottles | Y |
| Device charger | Battery charging | Y |
| Charger Connector | Connection of charger to device | Y |
| TOP PLATE with maintenance key | Closing device | Y |
| Dosing Door | | Y |
| Mounting set (metal parts, screws etc) | | |
| Hinges (top plate, dosing door, spare dose door) | | |

Figure 4:
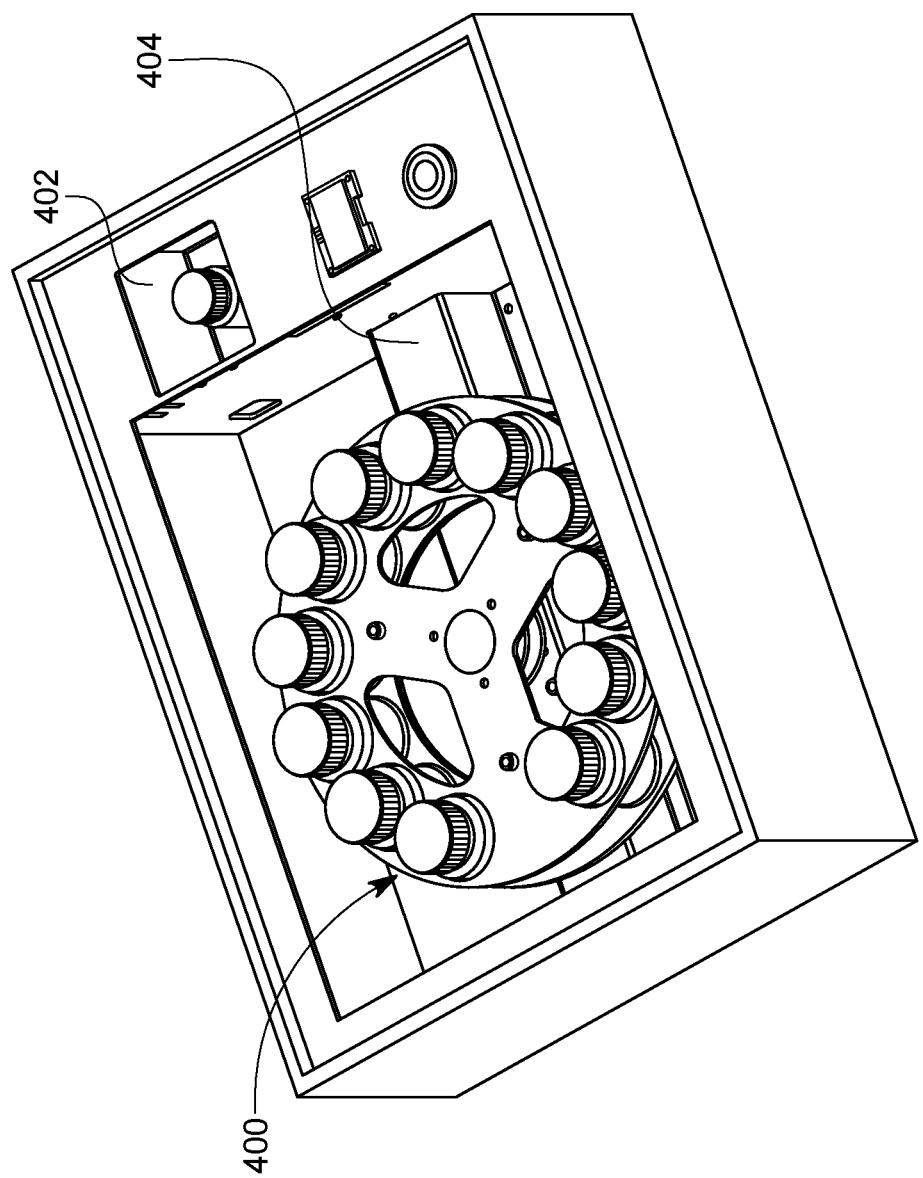
FIG. 4 depicts the network-enabled lockbox assembly of FIG. 3 with the carousel cover and the static dose dispensing lid removed according to an embodiment of the subject matter described herein.

FIG. 4 depicts a network-enabled lockbox for remote medications management with the lid open and the static dose dispensing lids in an open position according to an embodiment of the subject matter described herein. Referring to FIG. 4, carousel 400 is shown fully loaded with 12 doses, a blank dosing position, and a static dose 402. The carousel 400 may be rotated by means of a motor assembly 404 located below the carousel 400. The motor assembly 404 may rotate a central shaft connected to a central hole in the carousel 400. This allows the carousel to be rotated such that a desired dose at a particular dosing position can be moved beneath the primary dosing door during the DW. Outside of the DW, the blank position of the carousel, where no dose is located, may be positioned beneath the primary dosing door. At each subsequent DW, a next dose may be moved beneath the primary dosing door.

In another embodiment, the dosing door may be configured to rotate over the carousel such that a desired dose at a particular dosing position can be moved beneath the primary dosing door during the DW. In such an embodiment the dosing door may be installed on a circular plate and rotated by the motor assembly over a fixed carousel.

In another embodiment, the carousel 400 (or components thereof) may be manufactured using 3D printing or other additive manufacturing techniques. 3D printing may allow for per-carousel customizations that are not economically feasible using other manufacturing techniques such as die- or laser-cutting sheets of metal.

Figure 5:
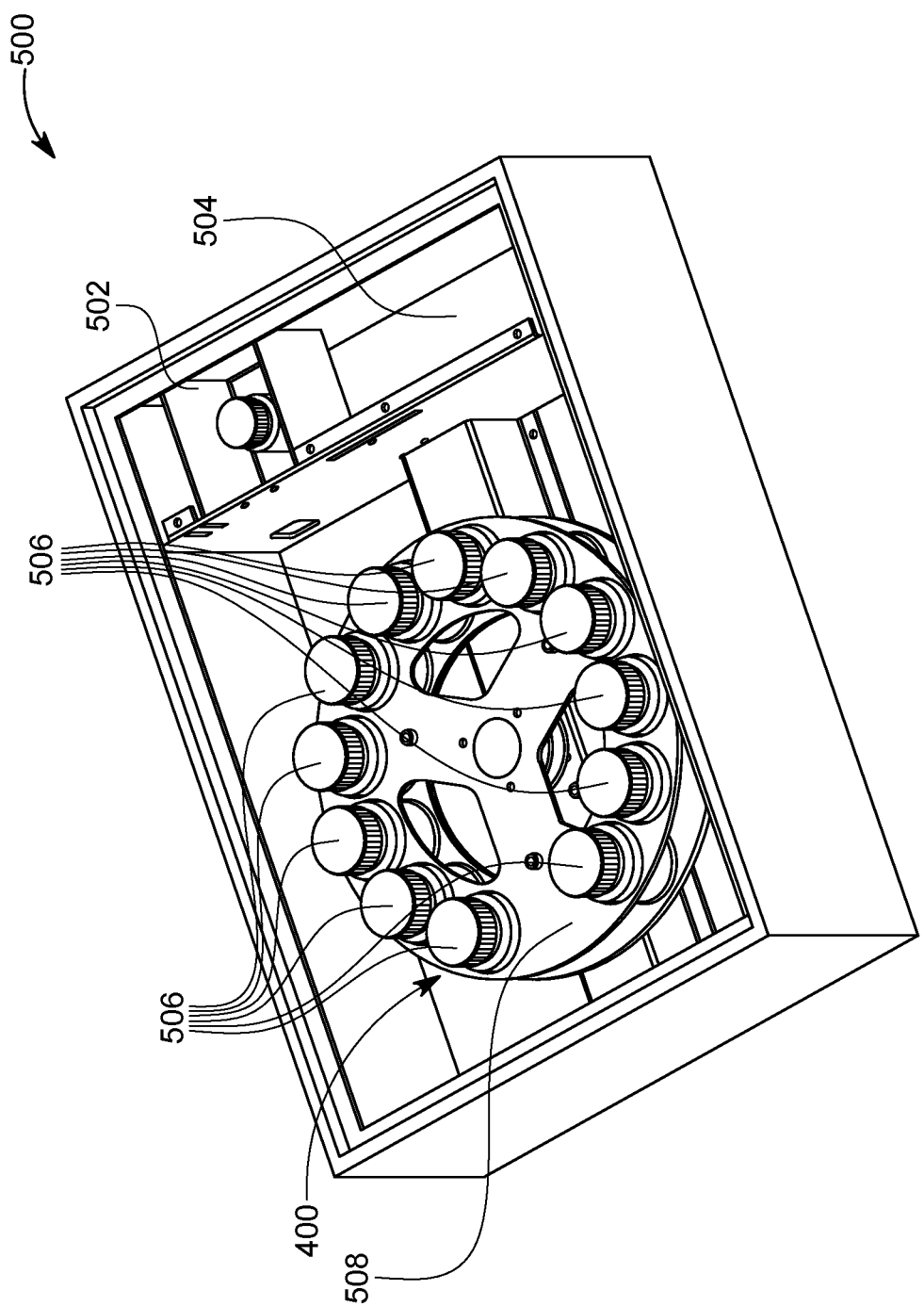
FIG. 5 depicts a perspective view of the network-enabled lockbox assembly of FIG. 3 with the entire top plate removed thereby exposing the subdivided interior portions of the assembly according to an embodiment of the subject matter described herein.

FIG. 5 depicts a perspective view of a network-enabled lockbox assembly with the entire top plate removed thereby exposing the subdivided interior portions of the assembly according to an embodiment of the subject matter described herein.

The network-enabled lockbox assembly shown in FIG. 5 may include an interior volume that is subdivided into several smaller volumes. For example, the carousel 400 may be located in a carousel portion 500, the static dose 402 may be located in a static dose portion 502, and various electronics may be located in an electronics portion 504.

The carousel 400 may include a plurality of dosing positions 506 that are loaded with a corresponding number of vials. After initial loading and before the first dose is taken, each of the vials in the dosing positions 506 may contain a dose. At each DW, the patient removes a vial, consumes the dose of the controlled substance contained therein, and replaces the empty vial to the same dosing position in the carousel. Thus, dispensing on the number of doses previously consumed, the vials shown in FIG. 5 may contain a varying number of actual doses. Here, the carousel includes 12 dosing positions 506 and a blank position 508. While the blank position 508 is optional, the blank position provides for additional security because the carousel 400 may be rotated between DWs such that the blank position 508 is located beneath the primary dosing door. Therefore, in the event that the primary dosing door is opened outside of a DW, the user cannot gain access to a vial/dose.

In another embodiment, each position 506 in the carousel 400 could hold multiple pills in a holder. The holder could be configured to count and report, to the device 100, a number of pills dispensed and a number of pills remaining. By allowing for a variable number of pills in each dosing position 506, the dosing schedule for a patient may be more flexible and customized than a configuration in which a single pill is located in each dosing position 506. The holder may count and report the number of pills, for example, using a camera sensor and/or a weight sensor to either visually identify the number of pills or to compare a weight of the pills remaining with known values of the initial weight of the pills in the holder and the weight of each pill individually.

In one embodiment, sensors are configured to directly detect what is dispensed rather than inferring what is dispensed based on detecting the presence or absence of a physical object such as a vial or bottle. For example, in contrast to simply detecting that a bottle containing 5 ml of liquid was removed from the carousel during the dosing window and then replaced back to the carousel, thereby inferring that the 5 ml of liquid (dose) was consumed, in some embodiments the presence or absence of the liquid dose in the bottle can be directly detected. In one example, this may include using a weight sensor for comparing the weight of the bottle before and after being removed from the carousel during the dosing window. A preconfigured weight for the bottle and the liquid may be used to determine whether the liquid was consumed. In another example, a camera sensor may visually detect a volume of liquid in the bottle. This may be easiest when a clear bottle and a colored liquid are used. Other types of direct detection sensors may also be used without departing from the scope of the subject matter described herein.

It is appreciated that the various sensors in the network-enabled lockbox may communicate internally with other sensors and/or with external devices such as the remote server or a mobile phone. For example, multiple weight sensors, motion sensors, etc. may communicate with other sensors of the same type or different types.

Figure 6:
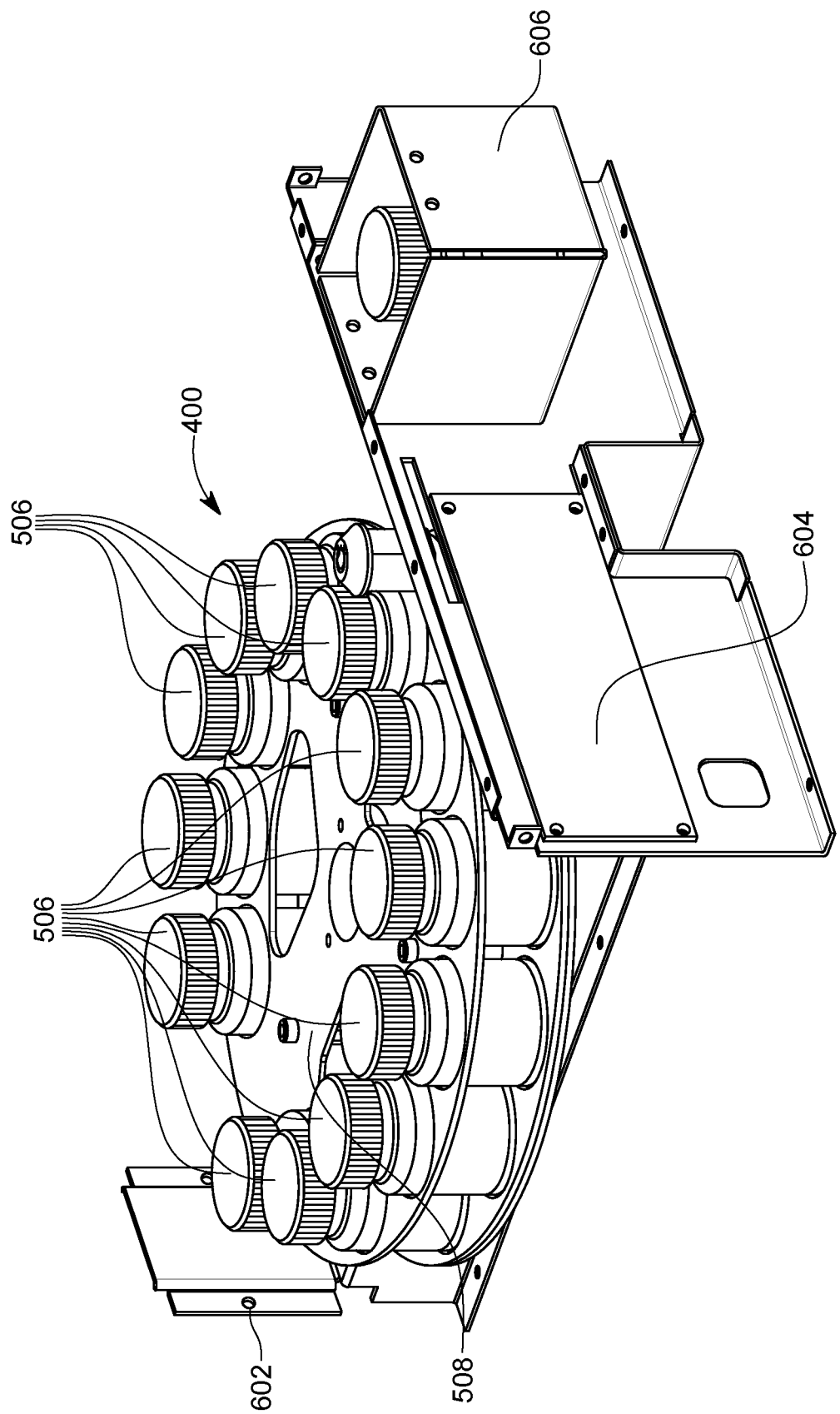
FIG. 6 depicts a perspective view of the carousel, motor, and worm drive assembly connected to an interior frame where the assembly is loaded with doses and a static dose according to an embodiment of the subject matter described herein.

FIG. 6 depicts a perspective view of the carousel, motor, and worm drive assembly connected to an interior frame where the assembly is loaded with doses and a static dose according to an embodiment of the subject matter described herein.

The loaded carousel and frame assembly 400 shown in FIG. 6 includes a first frame portion 602 for affixing or attaching to an interior wall of the lockbox 100 when inserted into the body 102. For example, the first frame portion 602 can be secured, affixed, or attached to the body 102 using one or more screws. This allows the carousel and frame assembly 400 to be assembled outside of the lockbox 100 and either removed or inserted into a lockbox 100 quickly and conveniently.

On the opposite side of the carousel, the carousel and frame assembly 600 includes a second frame portion 604 for affixing or attaching to an interior wall of the lockbox 100 when inserted into the body 102. Additionally, various components such as the motor, battery, communications subsystem, and/or control electronics may be attached to the second frame portion 604. This separates and divides the interior compartment space of the lockbox 100 to prevent tampering with these various components in the event that an unauthorized user gained access to the carousel portion of the lockbox 100.

Attached to the second frame portion 604 may be a static dose compartment 606 for storing a static dose. For example, the static dose compartment 606 may be a metal or plastic box with an open top portion that is sized to fully contain the static dose. When assembled with the top plate 200, the static dose access port lid 310 may be located directly above the open portion of the static dose compartment 606. The static dose can function as the either: 1) the last dose of a cycle; or, 2) as an emergency or safety dose such that the user still may obtain a dose in the event of a device malfunction, missing regular dose, or other issue.

Figure 7:
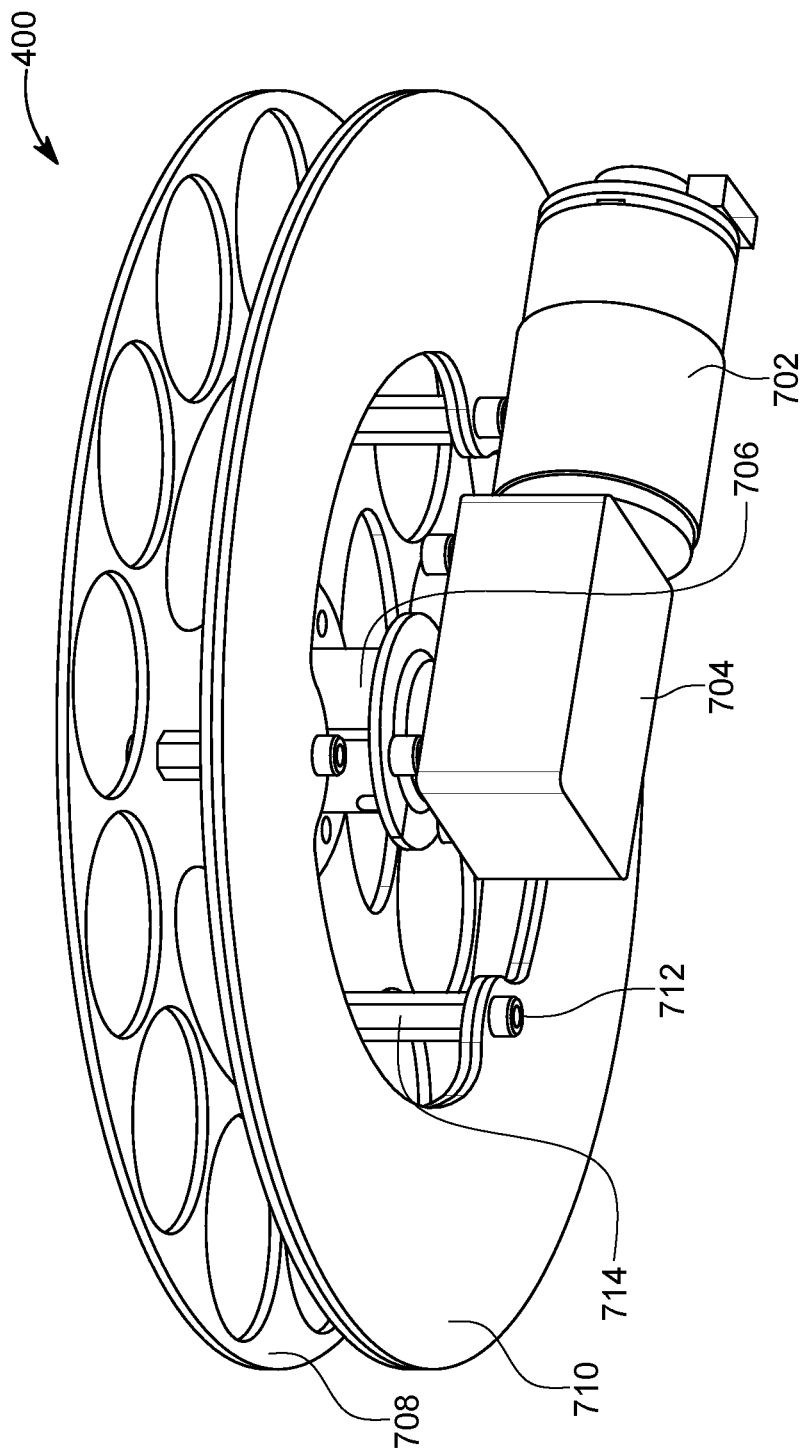
FIG. 7 depicts a perspective view of an empty carousel, motor, and worm drive without an internal frame according to an embodiment of the subject matter described herein.

FIG. 7 depicts a perspective view of an empty carousel, motor, and worm drive without an internal frame according to an embodiment of the subject matter described herein. The electric motor 702 is connected to an input shaft of the worm drive 704, a battery (not shown), and control electronics (not shown). The electric motor 702 is powered by the battery and drives the input shaft based on instructions from the control electronics. The worm drive 704 converts the rotational force of the input shaft to a rotational force of an output shaft 706. The output shaft 706 of the worm drive 704 may be vertically oriented and located within a central hole of the carousel 400. It is appreciated that in other embodiments, not shown, the worm drive 704 may instead include a stepper motor and gear and/or a plurality of braking solenoids. The worm drive 704 may, however, be cheaper and easier to manufacture than a stepper motor because the worm drive 704 does not need separate gearing and encoding components. Additionally, the worm gear ratio prevents carousel turning when the motor is not energized, removing cost of braking solenoids and alignment issues of the carousel in operation with the braking solenoids.

The carousel 400 includes a top plate 708 and a bottom plate 710, each comprising a circular disc of a solid, rigid material.

The bottom plate 710 has an inner diameter and an outer diameter where a solid material is located between the inner and outer diameters. The bottom plate 710 also has a plurality of screw holes 712 for receiving a plurality of standoff screws 714 that securely attach the bottom plate 710 to the top plate 708 in a parallel configuration where the bottom plate 710 to the top plate 708 are distanced from one another by the length of the standoff screws 714.

The top plate 708 has also an inner diameter and an outer diameter where a solid material is located between the inner and outer diameters. In the example embodiment shown in FIG. 7, the outer diameters of the top plate 708 is the same or substantially the same as the outer diameter of the bottom plate 710. However, the inner diameter of the top plate 708 may be smaller than the inner diameter of the bottom plate 710 because the inner diameter of the top plate 708 is configured for receiving the output shaft from the worm drive 704.

The top plate 708 is also composed of a solid material located between the inner and outer diameters. In contrast to the bottom plate 710, the top plate 708 may include additional supports or solid material connecting an outer ring to a central hole. In one embodiment, the inner diameter of the top plate 708 may correspond to the diameter of the central hole for receiving the output shaft. In another embodiment, the inner diameter of the top plate 708 may be the same as the inner diameter of the bottom plate 710, with one or more connecting portions of the top plate 708. These connecting portions of the top plate 708 may be formed by removing solid material from the top plate 708 to create, for example, three roughly triangular and equally spaced openings that leave behind three roughly straight and equally spaced supports.

While the bottom plate 710 may be substantially solid between the inner and outer diameters, the top plate 708 includes a plurality of holes. Located between the inner and outer diameters of the top plate 708, there are a plurality of non-overlapping dispensing positions. Each dispensing position, except one, includes a hole in the top plate 708 for receiving, holding, storing, or securing a dose of the controlled substance. The remaining dispensing position is a blank position. There may be no hole in the top plate 708 located at the blank position. The dispensing positions may be equally spaced from each other. For example, the capacity of the carousel 400 may be 12 doses (plus one static dose that is located outside of the carousel and discussed later). The rotating carousel 400 can include one blank position which can be filled with a stub. The blank position, if configured, may be exposed in various conditions. For example, the blank position may be exposed after the carousel 400 refilled, before the first dose, and/or between doses. The top plate 708 may also include a plurality of screw holes 712 for receiving a plurality of standoff screws 714 for securely attaching the top plate to the bottom plate 710.

Figure 8:
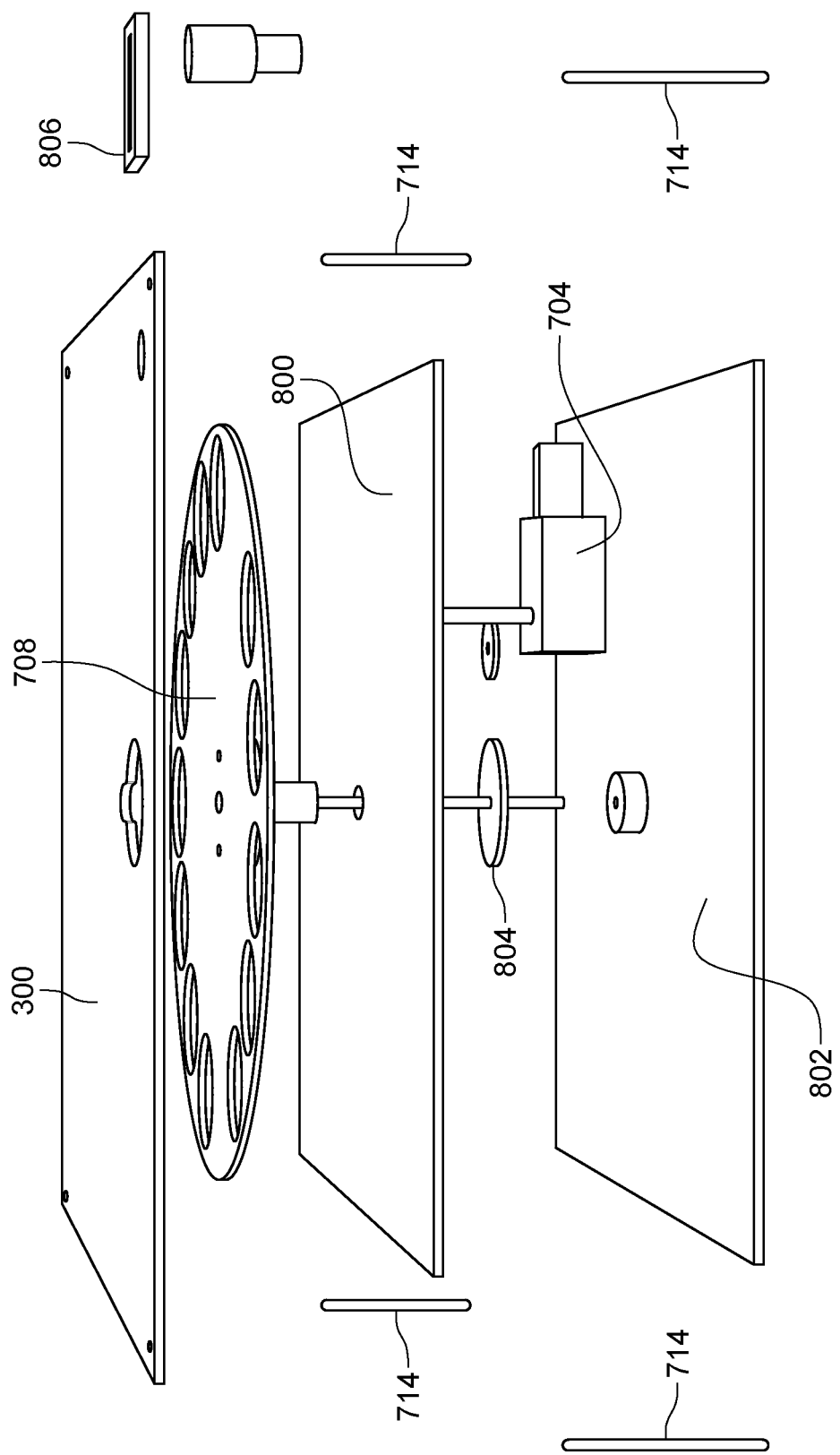
FIG. 8 depicts an exploded perspective view of an alternative configuration of an empty carousel, motor, and worm drive without an internal frame according to an embodiment of the subject matter described herein.

FIG. 8 depicts an exploded perspective view of an alternative configuration of an empty carousel, motor, and worm drive without an internal frame according to an embodiment of the subject matter described herein. In the embodiment shown, various components may be cut from sheets of aluminum. This may be easier to manufacture than other techniques. Carousel cover 300 may include a cutout portion for passing a dose from within the carousel to the user during a dosing window. Top plate 708 may include a plurality of circular cutouts corresponding to dosing positions for storing bottles of the controlled substance. The bottoms of the bottles of the controlled substance may be supported and slide on a middle plate 800. The middle plate 800 may be secured to a lower plate 802 via rotatable central shaft 804. A rotating bottom support plate 802 may avoid issues like sticking and be more compatible with "deactivation" schemes. The bottom two plates 800, 802 create wells for the bottle bottoms by having a ring-shaped plate with cut holes affixed flush above a solid ring. The two bottom plates 800, 802 are suspended by a series of standoffs similar to those shown as elements 714, where these standoffs rotate as integral components of the carousel. The carousel shown may be substantially cheaper to manufacture than other embodiments (i.e., less than $20), weigh less than one pound, and may be easily reconfigured to accommodate variable number of containers as well as containers of varying height and width.

Figure 9:
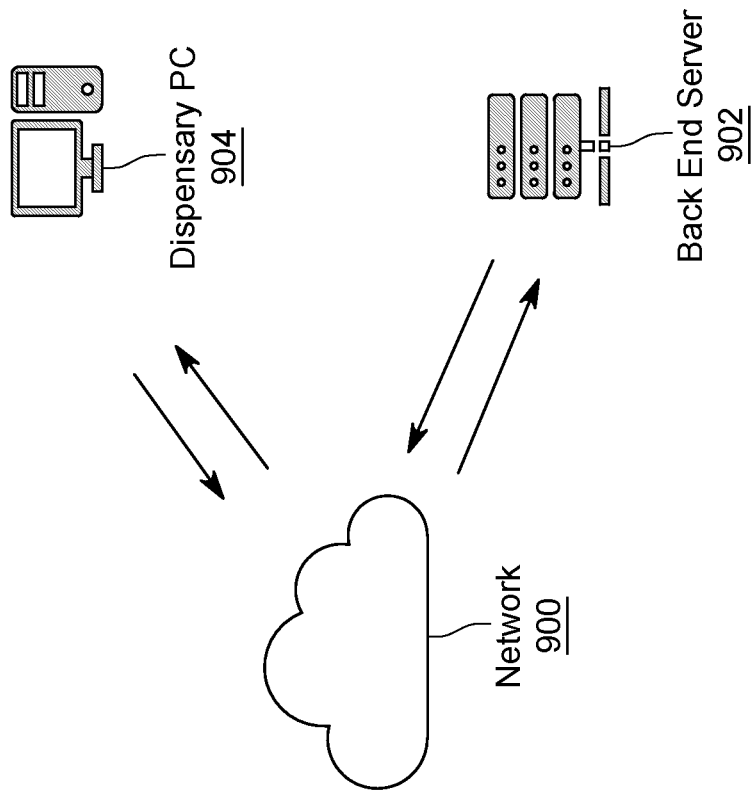
FIG. 9 depicts a network diagram illustrating exemplary communications between devices according to an embodiment of the subject matter described herein.
Figure 9:
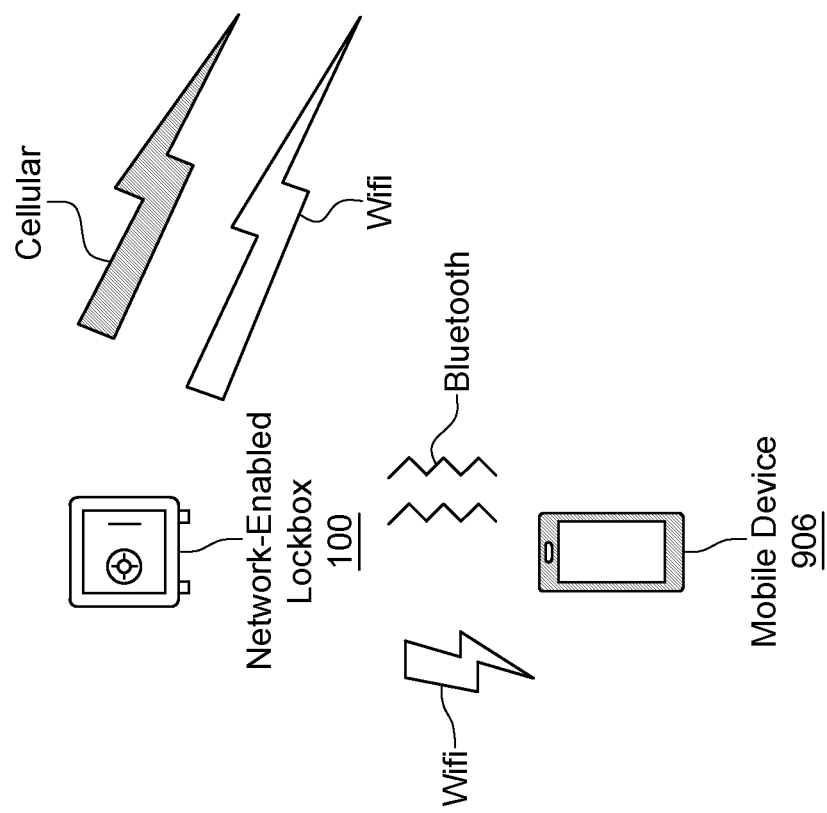

FIG. 9 depicts a network diagram illustrating exemplary communications between devices according to an embodiment of the subject matter described herein. The network-enabled lockbox 100 communicate with other devices using one or more networks and/or network protocols. Communications between the lockbox 100 and external devices may be handled by the communications subsystem in the lockbox 100. The communications subsystem communicates data between the plurality of sensors and/or the control electronics and a backend server or a mobile device. Typically, data is read from sensors and reported to an external device (e.g., backend server 902) while data is received from an external device for controlling various physical aspects of the lockbox 100, such as remotely locking the lockbox 100. The communications subsystem includes a Wi-Fi device for communicating with nearby digital devices to exchange data by radio waves via IEEE 802.11 wireless network protocols, a cellular radio for communicating wirelessly with cellular network towers, and a Bluetooth device for exchanging data between over short distances using UHF radio waves in the ISM bands from 2.402 GHz to 2.48 GHz.

The lockbox 100 may communicate, via network 800, with a backend server 902. Network 900 may include any combination of wired or wireless networks, such as a Wi-Fi router connected to the internet or a cellular tower connected to the internet. The backend server 902 may store reporting and analytics information for lockbox 100.

In general, the network 900 and/or, over which the client devices, the server 902 communicate, may be a cellular network, a broadband network, a telephonic network, an open network, such as the Internet, or a private network, such as an intranet and/or the extranet, or any combination thereof. For example, the Internet can provide file transfer, remote log in, email, news, RSS, cloud-based services, instant messaging, visual voicemail, push mail, VoIP, and other services through any known or convenient protocol, such as, but is not limited to the TCP/IP protocol, UDP, HTTP, DNS, FTP, UPnP, NSF, ISDN, PDH, RS-232, SDH, SONET, etc.

The network 900 and/or can be any collection of distinct networks operating wholly or partially in conjunction to provide connectivity to the client devices 100, 904, 906 and the server 902 and may appear as one or more networks to the serviced systems and devices 100, 904, 906. In one embodiment, communications to and from the client devices 100, 904, 906 can be achieved by, an open network, such as the Internet, or a private network, broadband network, such as an intranet and/or the extranet. In one embodiment, communications can be achieved by a secure communications protocol, such as secure sockets layer (SSL), or transport layer security (TLS).

Communications can be achieved via one or more networks 1000, such as, but are not limited to, one or more of WiMax, a Local Area Network (LAN), Wireless Local Area Network (WLAN), a Personal area network (PAN), a Campus area network (CAN), a Metropolitan area network (MAN), a Wide area network (WAN), a Wireless wide area network (WWAN), or any broadband network, and further enabled with technologies such as, by way of example, Global System for Mobile Communications (GSM), Personal Communications Service (PCS), Bluetooth, WiFi, Fixed Wireless Data, 2G, 2.5G, 3G (e.g., WCDMA/UMTS based 3G networks), 4G, IMT-Advanced, pre-4G, LTE Advanced, mobile WiMax, WiMax 2, WirelessMAN-Advanced networks, enhanced data rates for GSM evolution (EDGE), General packet radio service (GPRS), enhanced GPRS, iBurst, UMTS, HSPDA, HSUPA, HSPA, HSPA+, UMTS-TDD, 1×RTT, EV-DO, messaging protocols such as, TCP/IP, SMS, MMS, extensible messaging and presence protocol (XMPP), real time messaging protocol (RTMP), instant messaging and presence protocol (IMPP), instant messaging, USSD, IRC, or any other wireless data networks, broadband networks, or messaging protocols.

All communications may be initiated from the lockbox 100. The lockbox 100 may initiate communications that are "event" driven. Example events include: a dosing event, a dosing finished event, a dosing skipped event, a sensor threshold alarm, a shock event (e.g., free fall), a case opened event, and GPS activity.

In the absence of an event, communication between the lockbox 100 and the server 902 may be done with heartbeats. Heartbeats may be pre-scheduled and sent from the lockbox 100. The server 902 may be aware of the heartbeat schedule for the lockbox 100. A missed heartbeat may be interpreted by the server 902 as an indication that the remote lockbox 100 may have a problem, such as lack of communication and/or power or a security breach. A heartbeat may include local status and environmental data (e.g., temperature, humidity, location, battery state). In response, the lockbox 100 may receive status from the server 902 (for example, if a "lock" command is sent from the server 902 to the lockbox 100, the lockbox 100 will lock).

The client devices 100, 904, 906 can be any system and/or device, and/or any combination of devices/systems that is able to establish a connection, including wired, wireless, cellular connections with another device, a server and/or other systems such as server. Client devices 100, 904, 906 typically include a display and/or other output functionalities to present information and data exchanged between among the devices 100, 904, 906 and/or the server 902.

For example, the client device 906 can include mobile, hand held or portable devices, wireless devices, or non-portable devices and can be any of, but not limited to, a server desktop, a desktop computer, a computer cluster, or portable devices, including a notebook, a laptop computer, a handheld computer, a palmtop computer, a mobile phone, a cell phone, a smart phone, a PDA, a Blackberry device, a Palm device, any tablet, a "phablet" (a class of smart phones with larger screen sizes between a typical smart phone and tablet), a handheld tablet (e.g., an iPad, the Galaxy series, the Nexus, the Kindles, Kindle Fires, any Android-based tablet, Windows-based tablet, Amazon e-Readers or other readers, or any other tablet), any portable readers/reading devices, a hand held console, a hand held gaming device or console, a head mounted device, a head mounted display, a thin client or any SuperPhone such as the iPhone, and/or any other portable, mobile, hand held devices, or fixed wireless interface such as a M2M device, etc. In one embodiment, the client devices (or mobile device), host server, and application server are coupled via a network and/or a network. In some embodiments, the devices and host server may be directly connected to one another.

As referred to herein, the term "computing device" should be broadly construed. Examples would include a smart phone, a cell phone, a pager, a personal digital assistant (PDA, e.g., with GPRS NIC), a mobile computer with a cellular radio, or the like. A typical computing device is a wireless data access-enabled device (e.g., an iPHONE® smart phone, a BLACKBERRY® smart phone, a NEXUS ONE™ smart phone, an iPAD™ device, or the like) that is capable of sending and receiving data in a wireless manner using protocols like the Internet Protocol, or IP, and the wireless application protocol, or WAP. This allows users to access information via wireless devices, such as smart phones, mobile phones, pagers, two-way radios, communicators, and the like. Wireless data access is supported by many wireless networks, including, but not limited to, CDPD, CDMA, GSM, PDC, PHS, TDMA, FLEX, ReFLEX, iDEN, TETRA, DECT, DataTAC, Mobitex, EDGE and other 2G, 3G, 4G and LTE technologies, and it operates with many handheld device operating systems, such as PalmOS, EPOC, Windows CE, FLEXOS, OS/9, JavaOS, iOS and Android. Typically, these devices use graphical displays and can access the Internet (or other communications network) on so-called mini- or micro-browsers, which are web browsers with small file sizes that can accommodate the constrained operating environment of wireless devices on wireless networks. In a representative embodiment, the computing device is a cellular telephone or smart phone that operates over GPRS (General Packet Radio Services), which is a data technology for GSM networks. In addition to a conventional voice communication, a given computing device can communicate with another such device via many different types of message transfer techniques, including SMS (short message service), enhanced SMS (EMS), multi-media message (MMS), email WAP, paging, or other known or later-developed wireless data formats. Although many of the examples provided herein are implemented on a computing device, the examples may similarly be implemented on any suitable "computing device". An imaging device is any computing device operable to take or receive image data.

Initial Setup and Carousel Loading:

Device Setup: This may include physical assembly of the lockbox 100 by the manufacturer. As stated above, the internal frame and the carousel assembly, including the motor, battery, communications subsystem, control electronics etc. can be assembled outside of the lockbox body 102. The internal frame can be inserted into the body 102 and secured therein. The top plate 200 can then be added and secured, and the lid 104 attached to the body 102 and secured with lock 106.

Unique device ID: This may include assigning an identifier, such as an alphanumeric sequence, serial number, bar code, or QR code, that uniquely identifies a particular lockbox 100 from all other lockboxes. The unique device ID may be etched into the lockbox 100 itself, may be encoded into a memory in the lockbox 100, and may also be stored in a database associated with backend server 902.

Load Firmware: This may include installing the firmware permanently such that it cannot be changed after manufacture or may include programming a rewritable media after manufacture. Firmware is a type of software that is etched directly into a piece of hardware. It operates without going through APIs, the operating system, or device drivers—providing the needed instructions and guidance for the device to communicate with other devices or perform a set of basic tasks and functions as intended. Thus, firmware is a specific class of computer software that provides the low-level control for a device's specific hardware. Firmware may contain basic functions of a device and may provide hardware abstraction services to higher-level software such as operating systems. For less complex devices, firmware may act as the device's complete operating system, performing all control, monitoring and data manipulation functions. Firmware is held in non-volatile memory devices such as ROM, EPROM, EEPROM, and Flash memory. Updating firmware requires ROM integrated circuits to be physically replaced, or EPROM or flash memory to be reprogrammed through a special procedure. Some firmware memory devices are permanently installed and cannot be changed after manufacture.

Load SIM: This may include the initial programming of the SIM card to function with a particular cellular network provider and/or physical insertion of the programmed SIM card into an appropriate SIM card slot in the communications subsystem of the lockbox 100. A mobile network virtual operator (MVNO) may be used for IoT communications associated with the SIM cards. An MVNO is wireless communications services provider that does not own the wireless network infrastructure over which it provides services to its customers, and instead connects paired SIM cards to the best available network connection. Using an MVNO may significantly increase device connectivity across multiple geographies.

Run verification and validation (V&V): This may include procedures for checking that the network-enabled lockbox 100 and any associated front end or back-end software services and/or systems meet requirements and specifications and, further, that the network-enabled lockbox 100 fulfills its intended purpose of securely dispensing controlled substances. Verification checks that the network-enabled lockbox 100 meets a set of design specifications. In the development phase, verification procedures may involve performing special tests to model or simulate a portion, or the entirety, of the network-enabled lockbox 100 and then performing a review or analysis of the modeling results. In the post-development phase, verification procedures may involve regularly repeating tests devised specifically to ensure that the network-enabled lockbox 100 continues to meet the initial design requirements, specifications, and regulations as time progresses. Validation ensures that the network-enabled lockbox 100 (or portion thereof) meets the operational needs of the user. Tested attributes in validation tasks may include, but are not limited to, sensitivity and specificity, accuracy and precision, repeatability, reproducibility, and suitability of the network-enabled lockbox 100. Suitability tests the network-enabled lockbox 100 as a whole and is based on the concept that the equipment, electronics, and analytical operations constitute an integral system that can be evaluated as such.

Create Birth Certificate: This may include locating, identifying, scanning, or otherwise determining birth information for the patient. This information can be stored in a database associated with the back end server 902.

Charge Battery: This may include plugging the battery into an external power source in order to fully charge the battery. A single, full charge of the battery may allow the lockbox to operate the complete functionality of its sensors, communications subsystem, and control electronics for at least as long as the number of doses in the carousel. This allows a patient to use the lockbox for the entire two week period without having to plug in the device. However, in other embodiments, the battery may be larger or smaller such that a full charge lasts less than the two-week example dosing schedule. This may be because, for example, the weight of the battery is too heavy for a particular user or use case and there is sufficient external power to recharge the battery on-site or the electrical load produced by the sensors, communications subsystem, and control electronics exceeds an estimated amount such that the battery drains faster than estimated as well.

Assign to Customer: This may include assigning a particular network-enabled lockbox 100 to a particular patient or may include assigning multiple network-enabled lockboxes 100 to a particular clinic or dispensary. In either case, identifiers associated with either the clinic or the patient may be associated in a database with identifiers associated with one or more network-enabled lockboxes 100.

Device Configuration at Clinic: This may include loading a patient profile into memory, storage, or firmware of the network-enabled lockbox 100.

Connect to power: This may include plugging the battery into an external power source to fully charge the battery.

Assign to internal entity (e.g., Clinic #1): This may include associating the unique device ID with an identifier for a particular clinic or dispensary within a database.

Assign to Patient: This may include associating various data with a patient identifier in a database. The data may include a patient profile which is a collection of data associated with the patient. By organizing patient data into a patient profile, the data may be more easily and securely stored and handled. For example, a patient profile may be transferred from one client to another in the event that the patient moves. The patient profile may be transferred from a clinic computer to the lockbox 100 assigned to the patient. The patient profile may be modified at any time by authorized personnel. The patient profile may include, but is not limited to, the Patient ID, any prescriptions the patient is taking or has taken, dosing windows, and security rules.

The patient profile may also provide for inheritance in that some data within the patent profile (an object or class) may be based upon another object (prototype-based inheritance) or class (class-based inheritance), retaining similar implementation. Patient profile inheritance also provides for deriving new classes (i.e., sub classes) from existing classes and then forming them into a hierarchy of classes. In the patient profile, an object created through inheritance, a "child object", may acquire all the properties and behaviors of the "parent object".

Set user combination and record in database: This may include defining a code for locking and unlocking the built-in lock on a given lockbox 100. For example, a four-digit combination lock may be assigned a code 1234. The code assigned to the lockbox 100 may be stored in a database associated with back-end server 902.

Patient Ready V&V: This may include procedures for checking that the network-enabled lockbox 100 is ready to be given to the patient. For example, the patient may test that the built-in lock on the network-enabled lockbox 100 opens when the preconfigured code is entered. Similarly, the patient may test that the primary dispensing door opens when a test DW occurs.

Device Load/Unload at Clinic Dispensary: This may include placing the desired number of doses of the controlled substance into the desired number and locations within the carousel. For example, a carousel containing 12 regular dosing positions in the carousel and 1 static dose location in the static dose compartment may be loaded with 14 total doses such that every available dosing position is loaded. In another embodiment, the same carousel may be loaded with fewer doses than there are dosing positions. For example, 7 doses may be loaded in the 12-position carousel. This may be accomplished, for example, by loading all 7 doses sequentially starting at the first position or by loading each of the 7 doses in every other position. In either embodiment, it is appreciated that the software controlling the control electronics and for alerting the server 902 of various states of the lockbox 100 (e.g., dose taken, dose skipped, etc.) may require knowledge of the number and positions of the loaded doses within the carousel. This may be required in order to avoid misinterpretation by the lockbox 100 of a skipped dose when the carousel opens on an empty position that the software expects to be a loaded position. In other cases, the carousel may be programmed to skip a position each DW such that empty positions are skipped automatically. Again, this should be done in coordination with the reporting and analytics software. The loaded carousel and it associated components (motor, electronics, etc.) may be secured within the network-enabled lockbox 100 and the top plate and the lid may be secured.

Authenticate dispensary: This may include verifying information by the clinic or dispensary with a third-party in order to ensure that the entity loading the device is authenticated and authorized. If the dispensary were not authenticating, then a user could produce false reporting and analytics data regarding loading, unloading, dosing windows, etc.

Transfer assignment to dispensary: This may include transferring authority and control of the network-enabled lockbox 100 from the manufacturer to the clinic or dispensary.

Put in "load/unload mode" (Suspends security model): This may include the clinician or administrator temporarily suspending the normal security model that would otherwise alert of physical tampering of network-enabled lockbox 100 (e.g., removing the top plate, the carousel cover, or the carousel) in order to load or unload vials and/or the carousel.

Present patient prescription/order details to dispensary staff: This may include the patient providing prescription details regarding the controlled substance to be dispensed to dispensary staff. The prescription or order details may be provided electronically or on paper.

Open with key and Load/Unload: This may include opening the lid and/or the top plate using a key. The patient does not have access to this key. The patient gains access to the interior of the network-enabled lockbox 100 using a keyless lock and gains access to a vial using the primary dispending door. An administrator, however, may unlock the carousel cover 300 using a key to unlock keyed lock 304. This allows access to the entire carousel portion 500 for loading new vials and unloading used vials from the carousel 400.

Figure 10:
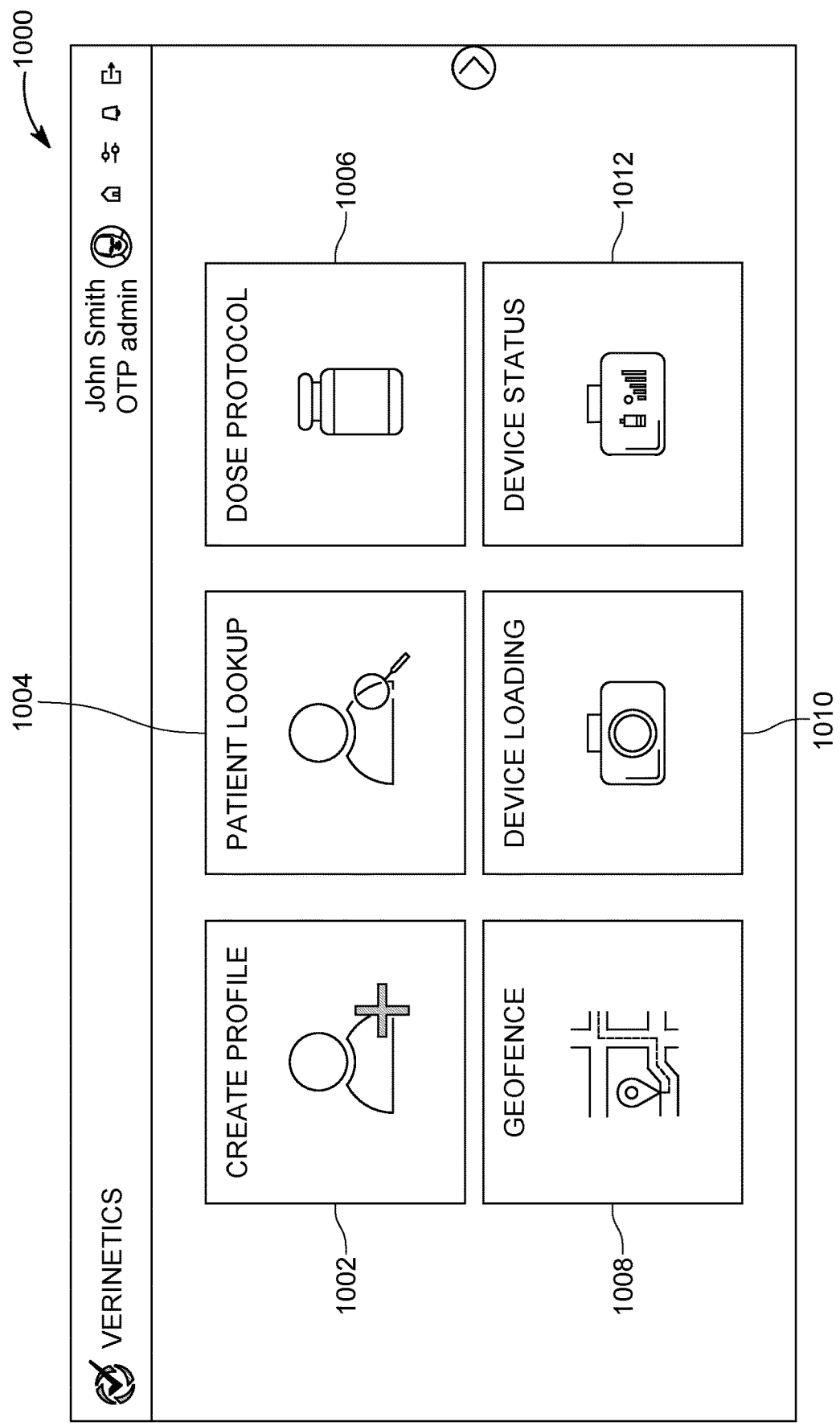
FIG. 10 depicts a graphical user interface for software executing on a computing device other than the network-enabled lockbox illustrating exemplary activity tiles design for an administrative dashboard according to an embodiment of the subject matter described herein.

FIG. 10 depicts a graphical user interface for software executing on a computing device other than the network-enabled lockbox illustrating exemplary activity tiles design for an administrative dashboard according to an embodiment of the subject matter described herein. Referring to FIG. 10, a user interface (UI) (e.g., a graphical user interface (GUI) or a command line interface) includes front end software for monitoring and administering one or more network-enabled lockboxes. FIG. 10 shows a wireframe illustration of a software visual interface (screen) for the administrator's view to the software. The interface includes a plurality of "activity tiles". Clicking on each activity tile opens a new, relevant window. The software is accessed by provider personnel having different roles in patient care. In one embodiment, there are dashboards tailored to each role. In one example role-function matrix, the dispensing nurse or pharmacists will have the primary role for software interactions.

Dashboard 1000 includes a "create profile" activity tile 1002, a "patient lookup" activity tile 1004, a "dose protocol" activity tile 1006, a "geofence" activity tile 1008, a "device loading" activity tile 1010, and a "device status" activity tile 1012. These tiles are not all required and additional tiles may be included in dashboard 1000 without departing from the scope of the subject matter described herein. The "create profile" activity tile 1002 allows an administrator to create a new patient profile. The patient profile may include information such as patient ID, home address, phone number, email address, case number, doctor, device ID, and device lock code. The "patient lookup" activity tile 1004 allows an administrator to search for a patient based on patient ID or other information in a patient profile. The "dose protocol" activity tile 1006 allows an administrator to view and manage a patient's medication, medication amount, and medication schedule. The "geofence" activity tile 1008 allows an administrator to identify and manage a geographical area within which a device 100 may be allowed or disallowed. If a device 100 leaves a geofenced area, an alert may be automatically generated and reported. The "device loading" activity tile 1010 allows an administrator to suspend various security and alerting measures that may be operable when the device is loaded and at home with the patient so that the device 100 can be loaded with doses without causing excessive or unnecessary alerts. The "device status" activity tile 1012 allows an administrator to view and manage various hardware statuses of the device 100 such as sensor data, battery levels, connected communications networks, etc.

Figure 11:
FIG. 11 depicts a graphical user interface for software executing on a computing device other than the network-enabled lockbox illustrating exemplary click-through result from the "Create Patient Profile" activity tile of FIG. 10 according to an embodiment of the subject matter described herein.

FIG. 11 depicts a graphical user interface for software executing on a computing device other than the network-enabled lockbox illustrating exemplary click-through result from the "Create Patient Profile" activity tile of FIG. 10 according to an embodiment of the subject matter described herein. As mentioned above, the patient profile may include information such as patient ID, home address, phone number, email address, case number, doctor, device ID, and device lock code.

Figure 12:
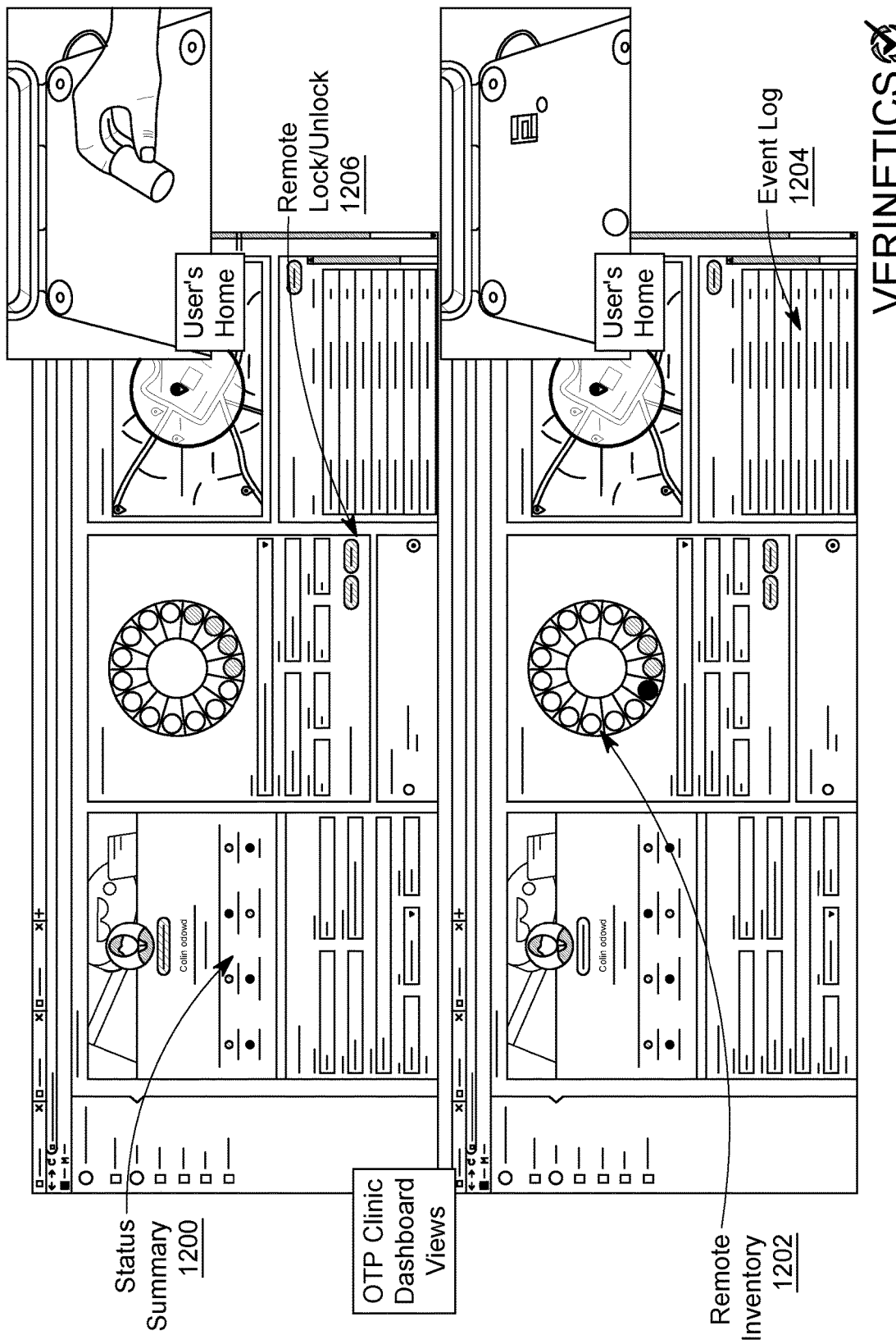
FIG. 12 depicts a graphical user interface for software executing on a computing device other than the network-enabled lockbox illustrating exemplary reporting, analytics, and administrative functions according to an embodiment of the subject matter described herein.

FIG. 12 depicts a graphical user interface for software executing on a computing device other than the network-enabled lockbox illustrating exemplary reporting, analytics, and administrative functions according to an embodiment of the subject matter described herein. Referring to FIG. 12, a user interface (UI) (e.g., a graphical user interface (GUI) or a command line interface) includes front end software for monitoring and administering one or more network-enabled lockboxes.

In a status summary portion 1200 of the UI, patient information may be displayed. The patient information may include some or all of the patient profile. The status of multiple patients may be displayed by selecting from among one or more dots, where a green dot may indicate an active patient and a red dot may indicate an inactive patient.

In a remote inventory portion 1202 of the UI, an illustration of a selected carousel may be displayed showing the dosing positions (labeled 0-14) where each dosing position may be colored to indicate a different status. For example, a dosing position may be colored grey (e.g., 0 and 5-14) to indicate that no dose is located at the position (e.g., previously consumed). A dosing position may be colored green (e.g., 2-4) to indicate that a dose is located at the position (e.g., not yet consumed). A dosing position may be colored red (e.g., 1) to indicate that the dose is the last dose. It is appreciated that in the embodiment shown, the first dose consumed during the first DW may correspond to dosing position 14 (assuming that position 0 is a blank position) and each successive DW may correspond to the next dosing position in decreasing order (e.g., 12, 11, 10 . . . ). Alternatively, however, the first dose consumed during the first DW may correspond to dosing position 1 (assuming that position 0 is a blank position) and each successive DW may correspond to the next dosing position in increasing order (e.g., 2, 3, 4, . . . ) without departing from the scope of the subject matter described herein.

In an event log portion 1204 of the UI, a record or history of alerts or events associated with a particular device ID may be displayed. Typically, the event log is presented in chronological order. However, the events in the event log may also be filtered and/or sorted by other metrics such as alphabetically, by type, date ranges, or manually searched.

In a remote lock/unlock portion 1206 of the UI, an administrator may determine whether a device is in a locked or unlocked state, as determined by one or more sensors located in the device. The administrator may also remotely lock or unlock the device by clicking a button in the interface. Additional security measures may be required, such as entering the device lock code associated with the patient profile for the device and/or an administrator login or confirmation before the remote lock/unlock request is performed.

The subject matter disclosed herein may be executed on a machine (computer system) within which a set of instructions, for causing the machine to perform any one or more of the methodologies discussed herein. The computer system includes a processor, memory, non-volatile memory, and an interface device. Various common components (e.g., cache memory) are omitted for illustrative simplicity. The computer system can be of any applicable known or convenient type.

The components of the computer system can be coupled together via a bus or through some other known or convenient device. The processor may be, for example, a conventional microprocessor such as an Intel Pentium microprocessor or Motorola power PC microprocessor. One of skill in the relevant art will recognize that the terms "machine-readable (storage) medium" or "computer-readable (storage) medium" include any type of device that is accessible by the processor. The memory is coupled to the processor by, for example, a bus. The memory can include, by way of example but not limitation, random access memory (RAM), such as dynamic RAM (DRAM) and static RAM (SRAM). The memory can be local, remote, or distributed.

Software is typically stored in the non-volatile memory and/or the drive unit. Indeed, for large programs, it may not even be possible to store the entire program in the memory. Nevertheless, for software to run, if necessary, it is moved to a computer readable location appropriate for processing, and for illustrative purposes, that location is referred to as the memory in this paper. Even when software is moved to the memory for execution, the processor typically make use of hardware registers to store values associated with the software, and local cache that, ideally, serves to speed up execution. As used herein, a software program is assumed to be stored at any known or convenient location (from non-volatile storage to hardware registers) when the software program is referred to as "implemented in a computer-readable medium." A processor is "configured to execute a program" when at least one value associated with the program is stored in a register readable by the processor.

In operation, the computer system can be controlled by operating system software that includes a file management system, such as a disk operating system. One example of operating system software with associated file management system software is the family of operating systems known as Windows® from Microsoft Corporation of Redmond, Washington, and their associated file management systems. Another example of operating system software with its associated file management system software is the Linux operating system and its associated file management system. The file management system is typically stored in the non-volatile memory and/or drive unit and causes the processor to execute the various acts required by the operating system to input and output data and to store data in the memory, including storing files on the non-volatile memory and/or drive unit.

The bus may couple the processor to the non-volatile memory and drive unit. The non-volatile memory is often a magnetic floppy or hard disk, a magnetic-optical disk, an optical disk, a read-only memory (ROM), such as a CD-ROM, EPROM, or EEPROM, a magnetic or optical card, or another form of storage for large amounts of data. Some of this data is often written, by a direct memory access process, into memory during execution of software in the computer. The non-volatile storage can be local, remote, or distributed. The non-volatile memory is optional because systems can be created with all applicable data available in memory. A typical computer system usually include at least a processor, memory, and a device (e.g., a bus) coupling the memory to the processor.

The bus may couple the processor to the network interface device. The interface can include one or more of a modem or network interface. It will be appreciated that a modem or network interface can be considered to be part of the computer system. The interface can include an analog modem, ISDN modem, cable modem, token ring interface, satellite transmission interface (e.g., "direct PC"), or other interfaces for coupling a computer system to other computer systems. The interface can include one or more input and/or output devices. The I/O devices can include, by way of example but not limitation, a keyboard, a mouse or other pointing device, disk drives, printers, a scanner, and other input and/or output devices, including a display device. The display device can include, by way of example but not limitation, a cathode ray tube (CRT), liquid crystal display (LCD), or some other applicable known or convenient display device. For simplicity, it is assumed that controllers of any devices not depicted in the Figures reside in the interface.

Some portions of the detailed description may be presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The algorithms and displays presented herein are not inherently related to any particular computer or other apparatus. Various general purpose systems may be used with programs in accordance with the teachings herein, or it may prove convenient to construct more specialized apparatus to perform the methods of some embodiments. The required structure for a variety of these systems will appear from the description below. In addition, the techniques are not described with reference to any particular programming language, and various embodiments may thus be implemented using a variety of programming languages.

In alternative embodiments, the machine operates as a standalone device or may be connected (e.g., networked) to other machines. In a networked deployment, the machine may operate in the capacity of a server or a client machine in a client-server network environment, or as a peer machine in a peer-to-peer (or distributed) network environment.

The machine may be a server computer, a client computer, a personal computer (PC), a tablet PC, a laptop computer, a set-top box (STB), a personal digital assistant (PDA), a cellular telephone, an iPhone, a Blackberry, a processor, a telephone, a web appliance, a network router, switch or bridge, or any machine capable of executing a set of instructions (sequential or otherwise) that specify actions to be taken by that machine.

While the machine-readable medium or machine-readable storage medium is shown in an exemplary embodiment to be a single medium, the term "machine-readable medium" and "machine-readable storage medium" should be taken to include a single medium or multiple media (e.g., a centralized or distributed database, and/or associated caches and servers) that store the one or more sets of instructions. The term "machine-readable medium" and "machine-readable storage medium" shall also be taken to include any medium that is capable of storing, encoding or carrying a set of instructions for execution by the machine and that cause the machine to perform any one or more of the methodologies of the presently disclosed technique and innovation.

In general, the routines executed to implement the embodiments of the disclosure, may be implemented as part of an operating system or a specific application, component, program, object, module or sequence of instructions referred to as "computer programs." The computer programs typically comprise one or more instructions set at various times in various memory and storage devices in a computer, and that, when read and executed by one or more processing units or processors in a computer, cause the computer to perform operations to execute elements involving the various aspects of the disclosure.

Moreover, while embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually effect the distribution.

Further examples of machine-readable storage media, machine-readable media, or computer-readable (storage) media include but are not limited to recordable type media such as volatile and non-volatile memory devices, floppy and other removable disks, hard disk drives, optical disks (e.g., Compact Disk Read-Only Memory (CD ROMS), Digital Versatile Disks, (DVDs), etc.), among others, and transmission type media such as digital and analog communication links.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The above detailed description of embodiments of the disclosure is not intended to be exhaustive or to limit the teachings to the precise form disclosed above. While specific embodiments of, and examples for, the disclosure are described above for illustrative purposes, various equivalent modifications are possible within the scope of the disclosure, as those skilled in the relevant art will recognize. For example, while processes or blocks are presented in a given order, alternative embodiments may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times. Further any specific numbers noted herein are only examples: alternative implementations may employ differing values or ranges.

The teachings of the disclosure provided herein can be applied to other systems, not necessarily the system described above. The elements and acts of the various embodiments described above can be combined to provide further embodiments.

Any patents and applications and other references noted above, including any that may be listed in accompanying filing papers, are incorporated herein by reference. Aspects of the disclosure can be modified, if necessary, to employ the systems, functions, and concepts of the various references described above to provide yet further embodiments of the disclosure.

These and other changes can be made to the disclosure in light of the above Detailed Description. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features, or aspects of the disclosure with which that terminology is associated. In general, the terms used in the following claims should not be construed to limit the disclosure to the specific embodiments disclosed in the specification, unless the above Detailed Description section explicitly defines such terms. Accordingly, the actual scope of the disclosure encompasses not only the disclosed embodiments, but also all equivalent ways of practicing or implementing the disclosure under the claims.

While certain aspects of the disclosure are presented below in certain claim forms, the inventors contemplate the various aspects of the disclosure in any number of claim forms. For example, while only one aspect of the disclosure is recited as a means-plus-function claim under 35 U.S.C. § 112, ¶ 6, other aspects may likewise be embodied as a means-plus-function claim, or in other forms, such as being embodied in a computer-readable medium. (Any claim intended to be treated under 35 U.S.C. § 112, ¶ 6 begins with the words "means for".) Accordingly, the applicant reserves the right to add additional claims after filing the application to pursue such additional claim forms for other aspects of the disclosure.

What is claimed is:

1. A device for remote medications management comprising:
   a plurality of vials each bearing a unique identifier and in discrete locations in the device;
   an alignment assembly for aligning one of the discrete locations with an access point for dispensing one of the plurality of vials;
   a computer readable memory comprising executable instructions for:
      selecting a vial of the plurality of vials to be dispensed;
      storing inventory information of the plurality of vials, wherein the inventory information associates the unique identifiers with a status for each the plurality of vials, the status selected from among the group indicating whether a vial is: loaded, dispensed, returned, or remaining undispensed in the device;
      receiving at least one signal from at least one of:
         an environmental sensor configured to detect at least one of: location, temperature, humidity, vibration, shock, and light intrusion; and
         a user-wearable physiological monitoring device in communication with the remote medications management device that is configured to monitor at least one of: a blood alcohol content (BAC), a heart rate, a blood pressure (BP), and an oxygenation state (pO2), and;
      determining, based on the at least one signal, whether a trigger condition for deactivation is detected, wherein the trigger condition is a physiological indicator of distress including at least one of: the BAC above a threshold level, the heart rate above a threshold level, the BP above a threshold level, and the pO2 below a threshold level; and
      deactivating dispensing of the vials from the device upon detecting the trigger condition;
   a deactivation assembly for deactivating dispensing of the vials based on the instructions stored in the computer-readable memory; and
   a communications subsystem operatively coupled to the computer-readable memory and configured to transmit an alert or notification to a remote recipient upon detecting the trigger condition.

2. The device of claim 1, wherein the discrete locations are fixed and the access point is movable.

3. The device of claim 1, wherein the discrete locations are movable and the access point is fixed.

4. The device of claim 3, wherein the movable discrete locations include storing the plurality of vials in a movable conveyor selected from the group: a carousel, a linear conveyor belt, or a serpentine conveyor belt.

5. The device of claim 1, wherein the deactivation assembly comprises a locking mechanism for prohibiting alignment of the access point with an unauthorized discrete location, where the locking mechanism is selected from the group: an escapement, a latching solenoid plunger, or a worm gear.

6. The device of claim 1, wherein the at least one source includes one or more sensors for detecting removal and return of a vial.

7. The device of claim 6, wherein the sensors further detect if a vial is full, empty, or partially full.

8. The device of claim 1, wherein the instructions further comprise an additional signal received from an additional source, the additional source being selected from the group: a GPS location, an onboard mobile network connection, a paired mobile device, an internet connection, a Bluetooth connection, an elapsed time measurement.

9. The device of claim 1, wherein the instructions further comprise an additional signal received from an additional source, the additional source being selected from the group: an acceleration sensor, an impact sensor, and a gyroscope.

10. The device of claim 1, wherein the environmental sensor is configured to detect at least one of: location, temperature, humidity, vibration, shock, and light intrusion.

11. The device of claim 1, wherein the communications subsystem is further configured to receive a command from the remote recipient to override or reinstate dispensing.

12. The device of claim 1, wherein the at least one signal includes a user-provided response, and the trigger condition includes the user-provided response indicating suicidal ideation.

13. The device of claim 1, wherein the at least one signal includes an electrocardiogram (ECG) of the user, and the trigger condition includes the ECG having at least one value outside of a predetermined range.

* * * * *